US011596554B2

(12) United States Patent
Selby et al.

(10) Patent No.: US 11,596,554 B2
(45) Date of Patent: Mar. 7, 2023

(54) FLEXIBLE NEGATIVE PRESSURE SYSTEM

(71) Applicant: ConvaTec Technologies Inc., Las Vegas, NV (US)

(72) Inventors: Robert Gordon Maurice Selby, Ryston (GB); Steven Paul Gowers, Royston (GB); Simon John Waddelow, Royston (GB); Marcus David Atkin, Royston (GB); Bryony Lee, Royston (GB); Duncan Gilding, Royston (GB); Stephen Bishop, Royston (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 973 days.

(21) Appl. No.: 16/316,025

(22) PCT Filed: Jul. 7, 2017

(86) PCT No.: PCT/US2017/041221
§ 371 (c)(1),
(2) Date: Jan. 7, 2019

(87) PCT Pub. No.: WO2018/009880
PCT Pub. Date: Jan. 11, 2018

(65) Prior Publication Data
US 2019/0159940 A1    May 30, 2019

Related U.S. Application Data

(60) Provisional application No. 62/360,233, filed on Jul. 8, 2016.

(51) Int. Cl.
*A61M 1/00* (2006.01)
*A61M 27/00* (2006.01)
(Continued)

(52) U.S. Cl.
CPC .... *A61F 13/0216* (2013.01); *A61F 13/00068* (2013.01); *A61M 1/90* (2021.05);
(Continued)

(58) Field of Classification Search
CPC .... A61M 1/00; A61M 27/00; A61M 2205/21; A61M 2205/3334; A61M 2205/3375;
(Continued)

(56) References Cited

U.S. PATENT DOCUMENTS 4,441,215 A     4/1984  Kaster
5,358,492 A    10/1994  Feibus
(Continued)

FOREIGN PATENT DOCUMENTS

EP    2711034 A1    3/2014
EP    2817038 A1   12/2014
(Continued)

OTHER PUBLICATIONS

Colombian Application No. NC2018/0005230 Office Action dated May 31, 2018.
(Continued)

*Primary Examiner* — Tatyana Zalukaeva
*Assistant Examiner* — Ilya Y Treyger
(74) *Attorney, Agent, or Firm* — Taft Stettinius & Hollister LLP; Ryan O. White; Derek B. Lavender

(57) ABSTRACT

Connectors and devices for flexible negative pressure systems are described.

20 Claims, 16 Drawing Sheets

(51) Int. Cl.
*A61F 13/02* (2006.01)
*A61F 13/00* (2006.01)
A61M 13/00 (2006.01)
A61B 17/50 (2006.01)

(52) U.S. Cl.
CPC .............. *A61M 27/00* (2013.01); *A61M 1/74* (2021.05); *A61M 2205/3344* (2013.01)

(58) Field of Classification Search
CPC ... A61M 2205/3379; A61M 2205/3389; A61F 13/00; A61F 13/02; A61B 17/50; G01F 23/2966; G01F 23/2967
See application file for complete search history.

(56) References Cited

U.S. PATENT DOCUMENTS

| | | | |
|---|---|---|---|
| 6,695,823 B1 | 2/2004 | Lina et al. |
| 8,083,712 B2 | 12/2011 | Biggie et al. |
| 8,308,714 B2 | 11/2012 | Weston et al. |
| 8,439,894 B1 | 5/2013 | Miller |
| 8,494,349 B2 | 7/2013 | Gordon |
| 8,521,979 B2 | 8/2013 | Laberge et al. |
| 8,814,840 B2 | 8/2014 | Evans et al. |
| 8,858,516 B2 | 10/2014 | Hu et al. |
| 9,205,183 B2 | 12/2015 | Hartwell et al. |
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Granberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |

(56) References Cited

U.S. PATENT DOCUMENTS

| | | |
|---|---|---|
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 10,828,404 B2 | 11/2020 | Vess et al. |
| 11,026,847 B2 | 6/2021 | Piotrowski et al. |
| 11,058,587 B2 | 7/2021 | Adie et al. |
| 11,058,588 B2 | 7/2021 | Albert et al. |
| 11,071,653 B2 | 7/2021 | Hunt |
| 11,083,631 B2 | 8/2021 | Dunn et al. |
| 11,090,195 B2 | 8/2021 | Adie et al. |
| 11,097,044 B2 | 8/2021 | Hartwell et al. |
| 11,110,010 B2 | 9/2021 | Hartwell |
| 11,116,669 B2 | 9/2021 | Gowans et al. |
| 11,123,474 B2 | 9/2021 | Hartwell |
| 11,141,521 B2 | 10/2021 | Beadle et al. |
| 11,147,714 B2 | 10/2021 | Blott et al. |
| 11,154,649 B2 | 10/2021 | Collinson et al. |
| 11,167,075 B2 | 11/2021 | Askem |
| 11,179,275 B2 | 11/2021 | Locke et al. |
| 11,179,276 B2 | 11/2021 | Hartwell |
| 11,197,953 B2 | 12/2021 | Heaton et al. |
| 11,207,217 B2 | 12/2021 | Locke et al. |
| 11,238,756 B2 | 2/2022 | Carroll et al. |
| 11,241,338 B2 | 2/2022 | Pratt et al. |
| 11,246,758 B2 | 2/2022 | Hardman et al. |
| 11,247,034 B2 | 2/2022 | Armstrong et al. |
| 11,253,399 B2 | 2/2022 | Hall et al. |
| 11,253,400 B2 | 2/2022 | Zochowski et al. |
| 11,266,537 B2 | 3/2022 | Robinson et al. |
| 11,266,774 B2 | 3/2022 | Selby et al. |
| 11,273,077 B2 | 3/2022 | Kubek |
| 11,278,454 B2 | 3/2022 | Edwards et al. |
| 11,351,064 B2 | 6/2022 | Hartwell |
| 11,364,150 B2 | 6/2022 | Gowans et al. |
| 11,364,151 B2 | 6/2022 | Hartwell |
| 11,376,356 B2 | 7/2022 | Weston |
| 11,382,796 B2 | 7/2022 | Long |
| 11,382,797 B2 | 7/2022 | Robinson et al. |
| 11,395,785 B2 | 7/2022 | Robinson et al. |
| 11,395,874 B2 | 7/2022 | Manwaring et al. |
| 11,413,193 B2 | 8/2022 | Kazala, Jr. et al. |
| 11,413,389 B2 | 8/2022 | Locke et al. |
| 11,419,767 B2 | 8/2022 | Dunn et al. |
| 11,419,768 B2 | 8/2022 | Cavanaugh, II et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0208300 A1 | 9/2007 | Pravong et al. |
| 2007/0219512 A1 | 9/2007 | Heaton et al. |
| 2007/0239078 A1 | 10/2007 | Jaeb |
| 2009/0082731 A1 | 3/2009 | Moreno |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0036333 A1 | 2/2010 | Schenk, III et al. |
| 2010/0069863 A1 | 3/2010 | Olson |
| 2010/0106116 A1 | 4/2010 | Knovles |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2010/0318043 A1 | 12/2010 | Malhi et al. |
| 2010/0324516 A1 | 12/2010 | Braga et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0152799 A1 | 6/2011 | Kevin et al. |
| 2011/0172616 A1 | 7/2011 | Hartwell et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0268851 A1 | 11/2011 | Locke |
| 2011/0275972 A1 | 11/2011 | Rosenberg |
| 2011/0276016 A1 | 11/2011 | Tsai |
| 2011/0288512 A1 | 11/2011 | Locke et al. |
| 2012/0016322 A1 | 1/2012 | Coulthard et al. |
| 2012/0065602 A1 | 3/2012 | Adams et al. |
| 2012/0071845 A1 | 3/2012 | Hu et al. |
| 2012/0100538 A1 | 4/2012 | Mikolajczyk et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0144234 A1 | 6/2013 | Croizat et al. |
| 2013/0226063 A1 | 8/2013 | Taylor et al. |
| 2013/0267918 A1 | 10/2013 | Pan et al. |
| 2013/0296816 A1 | 11/2013 | Greener |
| 2014/0005618 A1 | 1/2014 | Locke et al. |
| 2014/0031771 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276489 A1 | 9/2014 | Robinson et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2014/0336602 A1 | 11/2014 | Karpowicz et al. |
| 2014/0343519 A1 | 11/2014 | Weston |
| 2015/0018433 A1 | 1/2015 | Leipzig et al. |
| 2015/0057624 A1 | 2/2015 | Simmons et al. |
| 2015/0057625 A1 | 2/2015 | Coulthard |
| 2015/0071985 A1 | 3/2015 | Walker et al. |
| 2015/0073359 A1 | 3/2015 | Hudspeth et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |

(56) References Cited

U.S. PATENT DOCUMENTS

| | | |
|---|---|---|
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0182677 A1 | 7/2015 | Collinson et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0290364 A1 | 10/2015 | Wall et al. |
| 2015/0320901 A1 | 11/2015 | Chandrashekhar-Bhat et al. |
| 2015/0351970 A1 | 12/2015 | Dagger et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0151547 A1 | 6/2016 | Hartwell et al. |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |

(56) References Cited

U.S. PATENT DOCUMENTS

| | | |
|---|---|---|
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |

(56) References Cited

U.S. PATENT DOCUMENTS

| | | |
|---|---|---|
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0187171 A1 | 6/2021 | Collinson et al. |
| 2021/0187174 A1 | 6/2021 | Locke |
| 2021/0196524 A1 | 7/2021 | Locke et al. |
| 2021/0205143 A1 | 7/2021 | Locke et al. |
| 2021/0205527 A1 | 7/2021 | Pratt et al. |
| 2021/0228416 A1 | 7/2021 | Eriksson et al. |
| 2021/0228417 A1 | 7/2021 | Ha et al. |
| 2021/0244571 A1 | 8/2021 | Dunn |
| 2021/0260271 A1 | 8/2021 | Locke et al. |
| 2021/0275736 A1 | 9/2021 | Locke et al. |
| 2021/0290207 A1 | 9/2021 | Locke et al. |
| 2021/0290444 A1 | 9/2021 | Locke et al. |
| 2021/0290837 A1 | 9/2021 | Brandolini et al. |
| 2021/0338486 A1 | 11/2021 | Dagger et al. |
| 2021/0361854 A1 | 11/2021 | Askem et al. |
| 2021/0378876 A1 | 12/2021 | Gowans |
| 2021/0401628 A1 | 12/2021 | Gowans et al. |
| 2022/0000670 A1 | 1/2022 | Adie et al. |
| 2022/0000672 A1 | 1/2022 | Hunt |
| 2022/0000673 A1 | 1/2022 | Hartwell |
| 2022/0001096 A1 | 1/2022 | Locke et al. |
| 2022/0001098 A1 | 1/2022 | Hartwell et al. |
| 2022/0023527 A1 | 1/2022 | Beadle et al. |
| 2022/0031519 A1 | 2/2022 | Hardman et al. |
| 2022/0031933 A1 | 2/2022 | Askem |
| 2022/0031934 A1 | 2/2022 | Locke et al. |
| 2022/0047800 A1 | 2/2022 | Johannison et al. |
| 2022/0062060 A1 | 3/2022 | Hu et al. |
| 2022/0062526 A1 | 3/2022 | Heaton et al. |
| 2022/0072215 A1 | 3/2022 | Hartwell |
| 2022/0080105 A1 | 3/2022 | Askem et al. |
| 2022/0096727 A1 | 3/2022 | Collinson et al. |
| 2022/0117794 A1 | 4/2022 | Hartwell et al. |
| 2022/0117795 A1 | 4/2022 | Adie et al. |
| 2022/0117796 A1 | 4/2022 | Adie et al. |
| 2022/0117797 A1 | 4/2022 | Adie et al. |
| 2022/0183894 A1 | 6/2022 | Mumby et al. |
| 2022/0193324 A1 | 6/2022 | Locke et al. |
| 2022/0218528 A1 | 7/2022 | Askem et al. |
| 2022/0226160 A1 | 7/2022 | Hartwell |
| 2022/0226162 A1 | 7/2022 | Daich et al. |
| 2022/0241113 A1 | 8/2022 | Hall et al. |
| 2022/0257452 A1 | 8/2022 | Robinson et al. |

FOREIGN PATENT DOCUMENTS

| | | |
|---|---|---|
| EP | 3187204 A1 | 7/2017 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3829515 | 6/2021 |
| EP | 3836872 | 6/2021 |
| EP | 3852828 | 7/2021 |
| EP | 3852829 | 7/2021 |
| EP | 3866920 | 8/2021 |
| EP | 3871645 A1 | 9/2021 |
| EP | 3876885 | 9/2021 |
| EP | 3880143 | 9/2021 |
| EP | 3893825 | 10/2021 |
| EP | 3624741 B1 | 11/2021 |
| EP | 3628289 B1 | 11/2021 |
| EP | 3096728 B1 | 12/2021 |
| EP | 3104816 B1 | 12/2021 |
| EP | 3322455 B1 | 12/2021 |
| EP | 3448451 B1 | 12/2021 |
| EP | 3651679 | 12/2021 |
| EP | 3939554 A1 | 1/2022 |
| EP | 3687467 B1 | 2/2022 |
| EP | 3796950 | 2/2022 |
| EP | 3740179 | 3/2022 |
| EP | 3586805 B1 | 4/2022 |
| EP | 4008299 A1 | 6/2022 |
| EP | 4008373 A1 | 6/2022 |
| EP | 2941231 B1 | 7/2022 |
| EP | 3372208 B1 | 7/2022 |
| EP | 3485922 B1 | 7/2022 |
| EP | 4023197 A1 | 7/2022 |
| EP | 2311509 B2 | 8/2022 |
| EP | 3574877 B1 | 8/2022 |
| EP | 4035636 A1 | 8/2022 |
| GB | 2579211 A | 6/2020 |
| GB | 2579368 A | 6/2020 |
| GB | 2589503 B | 6/2021 |
| GB | 2592804 A | 9/2021 |
| GB | 2592805 A | 9/2021 |
| JP | 2010531698 A | 9/2010 |
| JP | 2012528605 A | 11/2012 |
| WO | 2005018543 A2 | 3/2005 |
| WO | 2009004291 A2 | 1/2009 |
| WO | WO-2009106895 A1 | 9/2009 |
| WO | 2010141030 A1 | 12/2010 |
| WO | 2011121394 A1 | 10/2011 |
| WO | 2011135284 A1 | 11/2011 |
| WO | 2011144888 A1 | 11/2011 |
| WO | WO-2012057881 A1 | 5/2012 |
| WO | 2013015827 A2 | 1/2013 |
| WO | 2013126049 A1 | 8/2013 |
| WO | 2014014842 A1 | 1/2014 |
| WO | WO-2015052219 A1 | 4/2015 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | WO-2017068364 A1 | 4/2017 |
| WO | 2017125250 A1 | 7/2017 |
| WO | WO-2017196888 A1 | 11/2017 |

(56) References Cited

FOREIGN PATENT DOCUMENTS

| | | |
|---|---|---|
| WO | WO-2018009873 A1 | 1/2018 |
| WO | WO-2018009879 A1 | 1/2018 |
| WO | WO-2018009880 A1 | 1/2018 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |

OTHER PUBLICATIONS

Great Britain Application No. GB1608099.6 search report dated Oct. 11, 2016.
PCT/US2017/041221 International Search Report and Written Opinion dated Sep. 13, 2017.
PCT/GB2016/053295 International Preliminary Report on Patentability dated Apr. 24, 2018.
PCT/GB2016/053295 International Search Report and Written Opinion dated Jan. 17, 2017.
PCT/US2017/031817 International Search Report and Written Opinion dated Aug. 11, 2017.
PCT/US2017/031817 International Preliminary Reporton Patentability dated Nov. 13, 2018.
PCT/US2017/041208 International Search Report and Written Opinion dated Sep. 8, 2017.
PCT/US2017/041216 International Search Report and Written Opinion dated Sep. 13, 2017.
PCT/US2017/041208 International Preliminary Report on Patentability dated Jan. 8, 2019.
PCT/US2017/041216 International Preliminary Report on Patentability dated Jan. 8, 2019.
PCT/US2017/041221 International Preliminary Report on Patentability dated Jan. 8, 2019.
Extended European Search Report and Written Opinion for EP17825036; dated Feb. 21, 2020; 8 Pages.
Office Action Summary; Japanese Patent Office; Japanese Application No. 2019-500496; dated Sep. 7, 2021; 6 pages.

FLEXIBLE NEGATIVE PRESSURE SYSTEM

CROSS-REFERENCE

This application is a U.S. National Phase of International Application No. PCT/US2017/041221, filed on Jul. 7, 2017, which claims the benefit of U.S. Provisional Application No. 62/360,233, filed Jul. 8, 2016, both of which are incorporated herein by reference in their entirety.

BACKGROUND OF THE INVENTION

Wounds may be treated by providing negative pressure to the space above the wound to promote healing in a process often referred to as negative pressure wound therapy (NPWT). During NPWT, effluent such as exudates are removed from the wound and collected. In some therapies, the effluent is stored in a canister positioned between the source of negative pressure and a transfer dressing providing the space above the wound. In other therapies, the effluent is stored within an absorbing dressing provided in the space above the wound.

SUMMARY OF THE INVENTION

Medical procedures often involve the removal of fluid or wound exudate from a patient including, for example, during negative pressure wound therapy (NPWT). For NPWT, fluid such as exudates may be collected in a dressing positioned over the wound and/or in a canister. For many patients undergoing NPWT, exudate collection needs change during treatment such that a canister is used to collect fluid in a first part of the treatment, and an absorbing dressing is used to collect exudates in a second part of the treatment. A device that could adapt to the changing needs of the patient during NPWT would provide a cost benefit to the healthcare community by allowing the same device to be used for a patient for a longer period than is typical for disposable NPWT devices. Further, such a device can simplify the process of discharging patients from a hospital by allowing the same device to be used and modified throughout treatment. Additionally, the device would also be able to treat a wider range of wounds than is typical for a disposable or single patient device.

In one aspect of the disclosure, provided herein are devices for use in negative pressure wound therapy, the devices comprising: (a) a first connection site, and (b) a connector comprising an air inlet fitting and an air pathway connecting an air outlet fitting and the air inlet fitting, wherein the air outlet fitting of the connector is coupled to the first connection site, wherein the connector is further selected from: (i) a first connector, wherein the air inlet fitting of the first connector is configured to connect with a first fluid retention source; and (ii) a second connector further comprising a fluid inlet fitting and a fluid outlet fitting connected by a fluid pathway, wherein the air inlet fitting and the fluid outlet fitting of the second connector are configured to connect with a second fluid retention source, and the fluid inlet fitting is configured to connect individually with a transfer dressing and a fluid retention dressing; wherein the first connector and second connector interchangeably connect to the first connection site of the device. In some embodiments, the air inlet fitting of the first connector connects to the first fluid retention source via an air supply tube. In some embodiments, the first fluid retention source is an absorbent wound dressing. In some embodiments, the fluid outlet fitting of the second connector is configured to connect with a fluid receiving fitting of the second fluid retention source. In some cases, the fluid outlet fitting of the second connector or the fluid receiving fitting of the second fluid retention source comprises a sealing member configured to provide a sealed connection between the second connector and the second fluid retention source. In some cases, the sealing member is an O-ring. In some embodiments, the fluid inlet fitting of the second connector is configured to connect with the transfer dressing via a fluid supply tube. In some cases, the fluid inlet fitting of the second connector is configured to connect with the fluid retention dressing via a fluid supply tube. In some cases, the fluid retention dressing comprises an absorbent material. In some embodiments, the air inlet fitting of the second connector is configured to connect with an air release fitting of the second fluid retention source. In some cases, the air inlet fitting of the second connector or the air release fitting of the second fluid retention source comprises a sealing member configured to provide a sealed connection between the second connector and the second fluid retention source. In some cases, the sealing member is an O-ring. In some embodiments, the fluid pathway of the second connector is configured to retain a liquid when the fluid outlet fitting of the second connector is not connected to the second fluid retention source. In some embodiments, the second fluid retention source is a canister.

In some embodiments, the length of the air pathway is between about 0.5 cm and about 2 cm. In some embodiments, the air outlet fitting is a push to connect fitting. In some embodiments, the air inlet fitting of the first connector is push to connect fitting. In some embodiments, the air inlet fitting of the second connector is a push to connect fitting. In some embodiments, the fluid inlet fitting of the second connector is a push to connect fitting. In some embodiments, the fluid outlet fitting of the second connector is a push to connect fitting. In some embodiments, the air outlet fitting is a male fitting. In some embodiments, the air inlet fitting of the first connector is a male fitting. In some embodiments, the air inlet fitting of the second connector is a female fitting. In some embodiments, the fluid outlet fitting of the second connector is a female fitting. In some embodiments, the fluid inlet fitting of the second connector is a male fitting. In some embodiments, the air outlet fitting or the first connection site comprises a sealing member configured to provide a sealed connection between the air outlet fitting and the first connection site. In some cases, the sealing member is an O-ring. In some embodiments, the first connection site comprises a female fitting.

In some embodiments, the device comprises a first compartment and a second compartment connected by the first connector or the second connector. In some cases, the first compartment comprises the first connection site. In some cases, the first connection site is configured to be in fluid communication with a source of negative pressure. In some cases, the first compartment comprises the source of negative pressure. In some cases, the source of negative pressure is a diaphragm pump. In some cases, the second compartment comprises a power source. In some embodiments, wherein the device comprises the first connector, the power source is configured to power a source of negative pressure from about 24 hours to about 30 days. In some embodiments, wherein the device comprises the second connector, the power source is configured to power a source of negative pressure from about 24 hours to about 60 days. In some cases, the power source comprises a battery. In some cases, the power source is removable from the second compartment. In some cases, the power source is replaceable. In some embodiments, the first compartment further comprises a controller for controlling operation of the source of negative pressure. In some embodiments, the first compartment is comprised of an injection mouldable plastic material. In some embodiments, the second compartment is comprised of an injection mouldable plastic material.

In some embodiments, the first connector, second connector, or both the first connector and second connector are comprised of an injection mouldable plastic material. In some embodiments, the length of the first connector and the second connector is from about 5 mm to about 40 mm. In some embodiments, the diameter of the air pathway is between about 0.5 mm and about 5 mm. In some embodiments, the air outlet fitting comprises an electrical contact.

In some embodiments, the device further comprises a second connection site configured to connect with a sensor outlet fitting of the first connector and a sensor outlet fitting of the second connector, wherein the first connector and second connector each further comprise a sensor inlet fitting and a sensor pathway connecting the sensor outlet fitting and the sensor inlet fitting. In some cases, the first connection site and the second connection site are positioned on a first side of the device. In some cases, the shortest distance between the center of the first connection site and the center of the second connection site is between about 1 mm and about 20 mm. In some embodiments, the sensor inlet fitting of the first connector is configured to connect with the first fluid retention source. In some cases, the sensor inlet fitting of the first connector connects to the first fluid retention source via a sensing line. In some embodiments, the sensor inlet fitting of the second connector is configured to connect with the transfer dressing via a sensing line. In some cases, the second connector is configured to connect with the fluid retention dressing via a sensing line. In some cases, fluid retention dressing comprises an absorbent material. In some embodiments, the length of the sensor pathway is between about 0.5 cm and about 2 cm. In some embodiments, the sensor outlet fitting is a push to connect fitting. In some embodiments, the sensor inlet fitting is a push to connect fitting. In some embodiments, the sensor outlet fitting is a male fitting. In some embodiments, the sensor inlet fitting is a male fitting. In some embodiments, the sensor outlet fitting or the second connection site comprises a sealing member configured to provide a sealed connection between the sensor outlet fitting and the second connection site. In some cases, the sealing member is an O-ring. In some embodiments, the second connection site comprises a female fitting. In some embodiments, the second connection site is configured to be in fluid communication with a pressure sensor. In some cases, a first compartment of the device comprises the pressure sensor. In some embodiments, the diameter of the sensor pathway is between about 0.5 mm and about 5 mm.

In another aspect of the disclosure, provided herein are connectors for use in negative pressure wound therapy with a canister, the connectors comprising a fluid inlet fitting connected by a fluid pathway to a fluid outlet fitting, and an air inlet fitting connected by an air pathway to an air outlet fitting; wherein the fluid outlet fitting is configured to be in fluid communication with the air inlet fitting upon joining the fluid outlet fitting and the air inlet fitting to the canister. In some embodiments, the fluid outlet fitting is configured to connect with a fluid receiving fitting of the canister. In some cases, the fluid outlet fitting of the connector or the fluid receiving fitting of the canister comprises a sealing member configured to provide a sealed connection between the connector and the canister. In some embodiments, the air inlet fitting is configured to connect with an air release fitting of the canister. In some cases, the air inlet fitting of the connector or the fluid receiving fitting of the canister comprises a sealing member configured to provide a sealed connection between the connector and the canister. In some cases, the sealing member is an O-ring. In some embodiments, the fluid inlet fitting is configured to connect with a transfer dressing. In some cases, the fluid inlet fitting is configured to connect with a fluid retention dressing. In some cases, the fluid retention dressing comprises an absorbent material.

In some embodiments, the connector further comprises a sensor inlet fitting connected to a sensor outlet fitting by a sensor pathway. In some embodiments, the fluid pathway is configured to retain a liquid when the fluid outlet fitting and air inlet fitting are not joined to the canister. In some cases, the fluid inlet fitting is a push to connect fitting. In some cases, the fluid outlet fitting is a push to connect fitting. In some cases, the air inlet fitting is a push to connect fitting. In some cases, the air outlet fitting is a push to connect fitting. In some cases, the fluid inlet fitting is a male fitting. In some cases, the fluid outlet fitting is a female fitting. In some cases, the air inlet fitting is a female fitting. In some cases, the air outlet fitting is a male fitting.

In some embodiments, the air outlet fitting is configured to be in fluid communication with a source of negative pressure upon connection of the air outlet fitting to a connection site of the negative pressure source. In some cases, the air outlet portion of the connector or the connection site of the negative pressure source comprises a sealing member configured to provide a sealed connection between the connector and the negative pressure source. In some cases, the sealing member is an O-ring. In some cases, the source of negative pressure is a diaphragm pump.

In some embodiments, the length of the connector is between about 5 mm and about 40 mm. In some embodiments, the width of the connector is between about 5 mm and about 20 mm. In some embodiments, the length of the air pathway is between about 0.5 cm and about 2 cm. In some embodiments, the length of the fluid pathway is between about 0.5 cm and about 2 cm. In some embodiments, the connector comprises an injection mouldable plastic material. In some embodiments, the diameter of the air pathway is between about 0.5 mm and about 5 mm. In some embodiments, the diameter of the fluid pathway is between about 0.5 mm and about 5 mm. In some embodiments, the air outlet fitting comprises an electrical contact. In some embodiments, the connector is part of a connecting device, the connecting device further comprising a power source. In some cases, the power source is configured to power a source of negative pressure from about 24 hours to about 60 days. In some cases, the power source comprises a battery. In some cases, the power source is removable from the second compartment. In some cases, the power source is replaceable.

Further provided are devices comprising the connector for use with a canister as described herein, and the canister. Further provided are devices comprising the connector for use with a canister as described herein, and a source of negative pressure. In some cases, the source of negative pressure is within a housing of a control unit. Further provided herein are devices comprising the connector for use with a canister as described herein and a transfer dressing and/or fluid retention dressing.

In another aspect of the disclosure, provided herein are connectors for use in negative pressure wound therapy with a fluid retention dressing, the connectors comprising an air inlet fitting connected by an air pathway to an air outlet fitting; wherein air inlet fitting is configured to connect with the fluid retention dressing and the air outlet fitting is configured to connect with a source of negative pressure such that a negative pressure applied from the source of negative pressure is received by the fluid retention dressing. In some embodiments, the length of the air pathway is between about 0.5 cm and about 2 cm. In some embodiments, the connector further comprises a sensor inlet fitting connected by a sensor pathway to a sensor outlet fitting. In some cases, the sensor inlet fitting is configured to connect with the fluid retention dressing. In some cases, the sensor outlet fitting is configured to connect with a pressure sensor. In some cases, the pressure sensor and/or source of negative pressure are housed in a control unit.

In some cases, the air inlet fitting is a push to connect fitting. In some cases, the air outlet fitting is a push to connect fitting. In some cases, the air inlet fitting is a male fitting. In some cases, the air outlet fitting is a male fitting. In some embodiments, the length of the connector is between about 5 mm and about 40 mm. In some embodiments, the width of the connector is between about 5 mm and about 20 mm. In some embodiments, the connector comprises an injection mouldable plastic material. In some embodiments, the diameter of the air pathway is between about 0.5 mm and about 5 mm. In some embodiments, the air outlet fitting comprises an electrical contact. In some embodiments, wherein the connector is part of a connecting device, the connecting device further comprising a power source. In some cases, the power source is configured to power a source of negative pressure from about 24 hours to about 30 days. In some cases, the power source comprises a battery. In some embodiments, the power source is removable from the second compartment. In some cases, the power source is replaceable. In some cases, the power source provides power to the source of negative pressure when the connector is connected to the source of negative pressure. In some embodiments, the source of negative pressure is a diaphragm pump.

Further provided are devices comprising the connector for use with a fluid retention dressing as described herein, and the fluid retention dressing. Further provided are devices comprising the connector for use with a fluid retention dressing as described herein, and a source of negative pressure. In some cases, the source of negative pressure is within a housing of a control unit. In some cases, the fluid retention dressing comprises a backing configured to create an enclosure between an interior surface of the backing and a wound for retaining fluid drawn from the wound during application of negative pressure. In some cases, the enclosure comprises an absorbent material.

In another aspect of the disclosure, provided herein are methods for replacing a fluid retention source during negative pressure wound therapy, the method comprising: (a) providing (i) a control unit comprising a source of negative pressure, a first connection site in fluid communication with the source of negative pressure, a sensor, and a second connection site in communication with the sensor; (ii) a first connector connected to the first connection site and the second connection site of the control unit; and (iii) a first fluid retention source connected to the first connector; (b) disconnecting the first connector from the control unit and the first fluid retention source, in either order; (c) connecting a second connector to a second fluid retention source and the first connection site and the second connection site of the control unit; wherein the second connector is connected to the second fluid retention source and control unit in either order; wherein the first connector and the second connector each comprise an air outlet fitting and an air inlet fitting connected by an air pathway, and a sensor outlet fitting and a sensor inlet fitting connected by a sensor pathway; wherein the first connection site of the control unit is connected to the air outlet fitting of the first connector in step (a) and the air outlet fitting of the second connector in step (c); wherein the second connection site of the control unit is connected to the sensor outlet fitting of the first connector in step (a) and the sensor outlet fitting of the second connector in step (c); and wherein the first fluid retention source is connected to the air inlet fitting of the first connector in step (a), and the second fluid retention source is connected to the air inlet fitting of the second connector in step (c). In some embodiments, the first fluid retention source is a first canister and the second fluid retention source is a second canister. In some cases, the first connector and the second connector each further comprise a fluid inlet fitting and a fluid outlet fitting connected by a fluid pathway; and wherein connection of the first canister to the first connector provides fluid communication between the fluid outlet fitting and the air inlet fitting of the first connector, and connection of the second canister to the second connector provides fluid communication between the fluid outlet fitting and the air inlet fitting of the second connector. In some cases, the fluid inlet fitting of the first connector is connected to a transfer dressing. In some cases, the fluid inlet fitting of the first connector is connected to a fluid retention dressing. In some cases, the first fluid retention source is a first absorbent dressing and the second fluid retention source is a second absorbent dressing. In some cases, the air inlet fitting of the first connector is connected to the first absorbent dressing by a first air supply tube and the air inlet fitting of the second connector is connected to the second absorbent dressing by a second air supply tube.

In some embodiments, the first fluid retention source is a canister and the second fluid retention source is an absorbent dressing. In some cases, the first connector further comprises a fluid inlet fitting and a fluid outlet fitting connected by a fluid pathway; and wherein connection of the canister to the first connector provides fluid communication between the fluid outlet fitting and the air inlet fitting of the first connector. In some cases, the fluid inlet fitting of the first connector is connected to a transfer dressing by a fluid supply tube. In some cases, the fluid inlet fitting of the first connector is connected to a fluid retention dressing by a fluid supply tube. In some cases, the air inlet fitting of the second connector is connected to the absorbent dressing by an air supply tube.

In some embodiments, the first fluid retention source is an absorbent dressing and the second fluid retention source is a canister. In some cases, the second connector further comprises a fluid inlet fitting and a fluid outlet fitting connected by a fluid pathway; and wherein connection of the canister to the second connector provides fluid communication between the fluid outlet fitting and the air inlet fitting of the first connector. In some cases, the fluid inlet fitting of the second connector is connected to a transfer dressing by a fluid supply tube. In some cases, the fluid inlet fitting of the second connector is connected to a fluid retention dressing by a fluid supply tube. In some cases, the air inlet fitting of the first connector is connected to the absorbent dressing by an air supply tube.

In some embodiments, the first connector, second connector, or both first connector and second connectors further comprise a fluid inlet fitting and a fluid outlet fitting connected by a fluid pathway. In some embodiments, the first connector is housed in a first connecting device and the second connector is housed in a second connecting device, the first connecting device and second connecting device each further comprising a power source. In some cases, the power source provides power to the source of negative pressure when the first connector and the second connector are connected to the control unit. In some cases, the air outlet of the first connector and the air outlet of the second connector each comprise an electrical contact for providing power to the control unit. In some cases, the method further comprises removing the power source from the first connecting device and recycling the power source. In some embodiments, wherein a liquid is located within the first connector, and when the first connector is disconnected from the first fluid retention source, the liquid is retained within the first connector.

DETAILED DESCRIPTION OF THE INVENTION

In one aspect of the disclosure, provided herein are devices configured to operate with both a canister for exudate collection when a wound is highly exudating and a higher capacity for exudate is needed, and an absorbing dressing which absorbs exudate to allow greater mobility for the patient. In some embodiments, the device comprises a housing configured to attach to two or more types of connectors, where one type of connector is configured to further attach to a canister and a first dressing, and the other type of connector is configured to further attach to second dressing. The first dressing is inclusive of transfer dressings in systems where exudate is primarily stored in the canister, as well as fluid retention dressings and absorbing dressings, where some fluid may be retained by the dressing and some fluid retained by the canister. The second dressing is generally a fluid retention dressing, such as an absorbent dressing, which retains exudates drawn out of the wound without necessitating use of a separate canister. The device may be configured so that selecting between the two operating modes is intuitive to the user and avoids multiple connection options that could be selected in error. In some embodiments, the connector configured for use with a canister and first dressing is packaged with a first dressing and/or canister. In some embodiments, the connector configured for use with a second dressing, such as an absorbing dressing, is packaged with a second dressing. In some embodiments, different connectors are configured such that only the correct connections to appropriate dressings can be made, mitigating potential multiple connection options selected in error.

In another aspect of the disclosure, devices provided herein optionally comprise a power source so that when the device is connected to a control unit comprising a source of negative pressure such as a pump, the power source provides power to the control unit. If the device and/or power source is replaceable, the control unit does not require the bulk of a power supply which would generally last the usable lifetime of the pump. Instead, multiple, smaller units of power are supplied to the control unit as needed. In this manner, the control unit is kept small, enhancing portability of a NPWT system.

Figure 1:
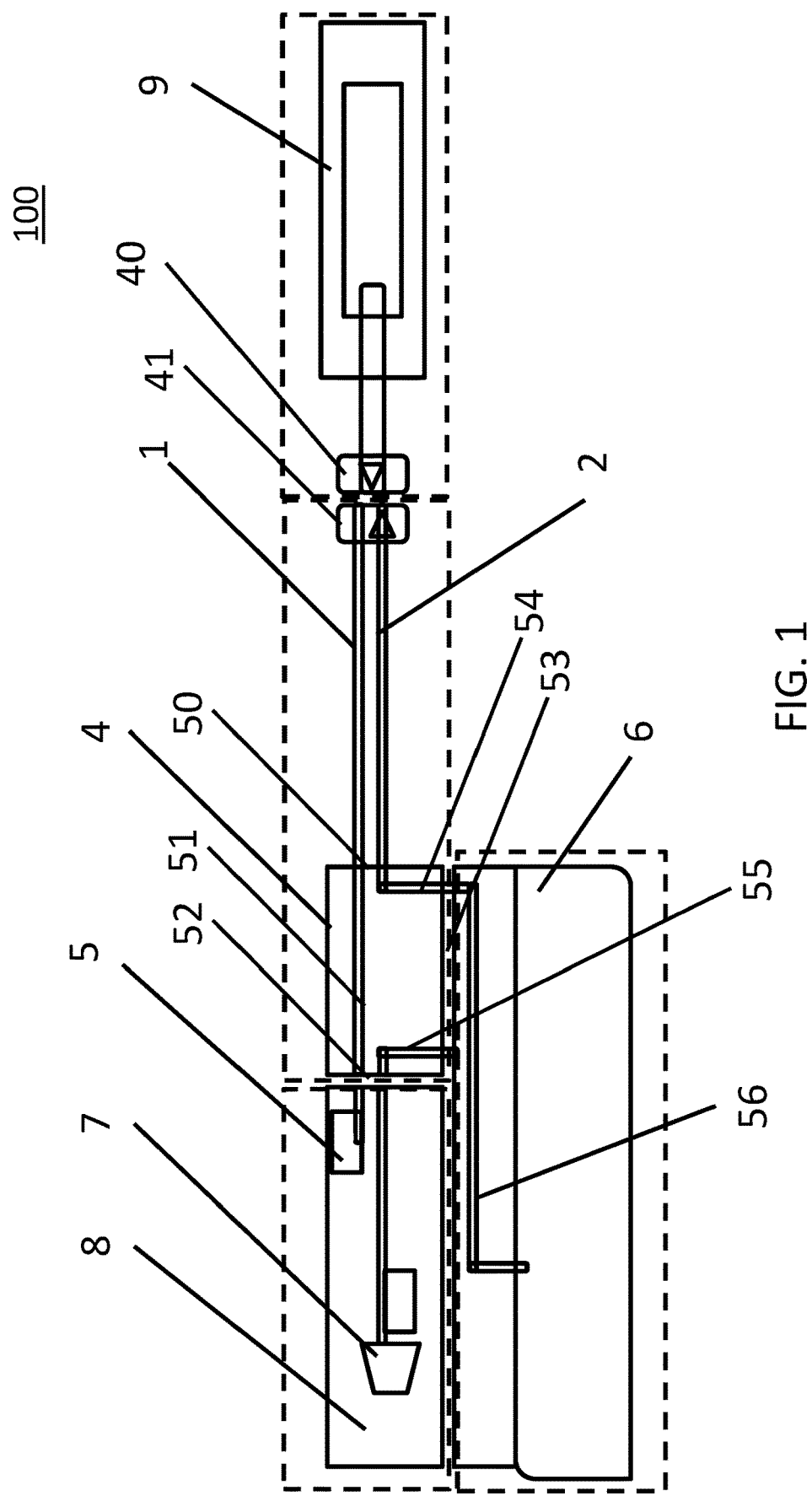
FIG. 1 shows an embodiment of a NPWT system comprising a connecting device 4 attached to a transfer dressing 9, a canister 6, and a control unit 8.
Figure 3:
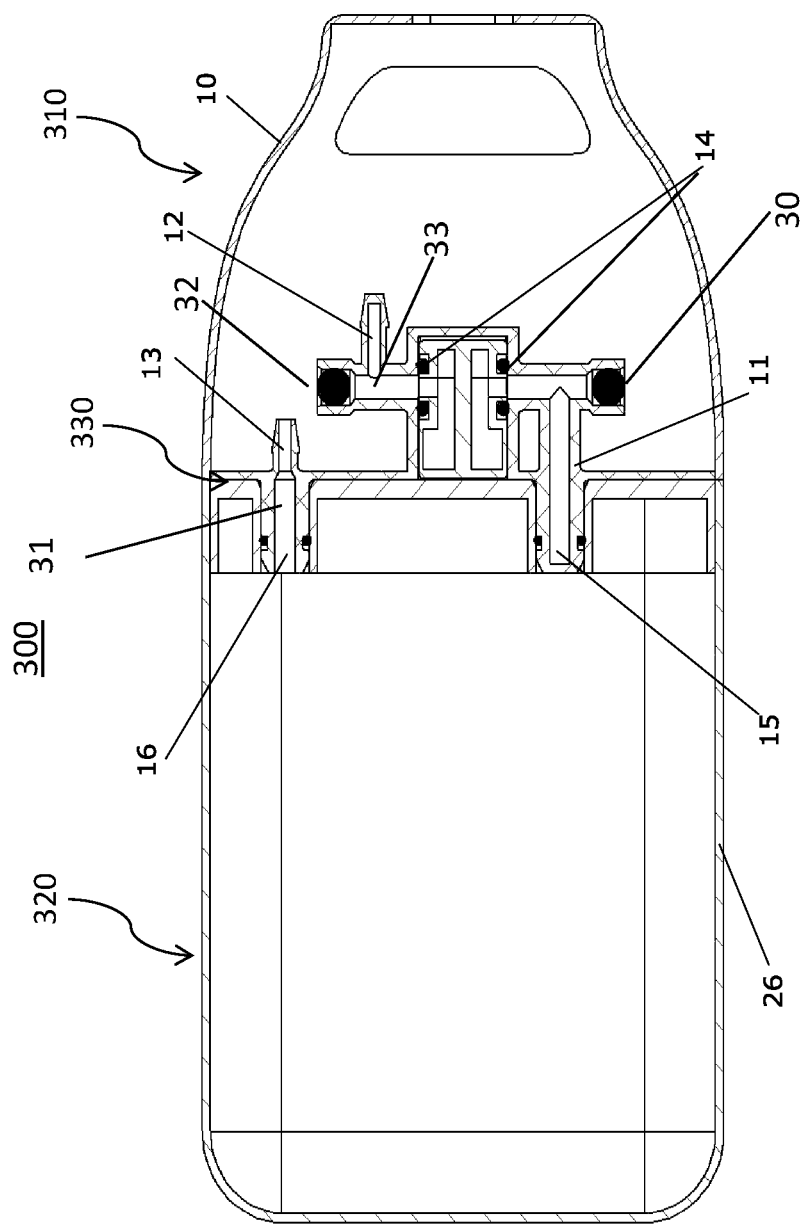
FIG. 3 shows a connecting device 310 joined to a control unit 320 of a NPWT system, where a connector 330 of the connecting device is configured to further join to a canister and a transfer dressing.

An embodiment of a NPWT system 100 comprising a connecting device 4 connecting a transfer wound dressing 9, a canister 6, and a control unit 8 is shown in FIG. 1. A detailed view of an embodiment of connecting device 4 is shown in FIG. 3 as 310, attached to an embodiment of a control unit 8 shown as 320. Referring to system 100, control unit 8 comprises a pump 7 for drawing exudate from a wound covered by transfer dressing 9 into canister 6 via connecting device 4. In other configurations, transfer dressing 9 is replaceable with a dressing having a capacity for retaining some fluid, such as an absorbing dressing.

Connecting device 4 is connected to the wound dressing 9 via a fluid supply tube 2 and a sensing line 1. A first end of fluid supply tube 2 and a first end of sensing line 1 are connected to connecting device 4 a first attachment portion 50 of the device. The second end of fluid supply tube 2 and the second end of sensing line 1 form an attachment region 41 that connects fluid supply tube 2 and sensing line 1 to an outlet 40 of transfer wound dressing 9.

Connecting device 4 is connected to canister 6 at a second attachment region 53 of the device. Connecting device 4 comprises a fluid pathway 54 to allow fluid to pass from the fluid supply tube 2 to canister 6 along pathway 56. Connecting device 4 further comprises an air pathway 55 to allow air to pass between canister 6 and control unit 8 via negative pressure supplied by pump 7.

Connecting device 4 is connected to control unit 8 at a third attachment region 52 of the device. Connecting device 4 comprises sensor pathway 51 to connect sensing line 1 and the pressure sensor 5 of the control unit 8.

Figure 4:
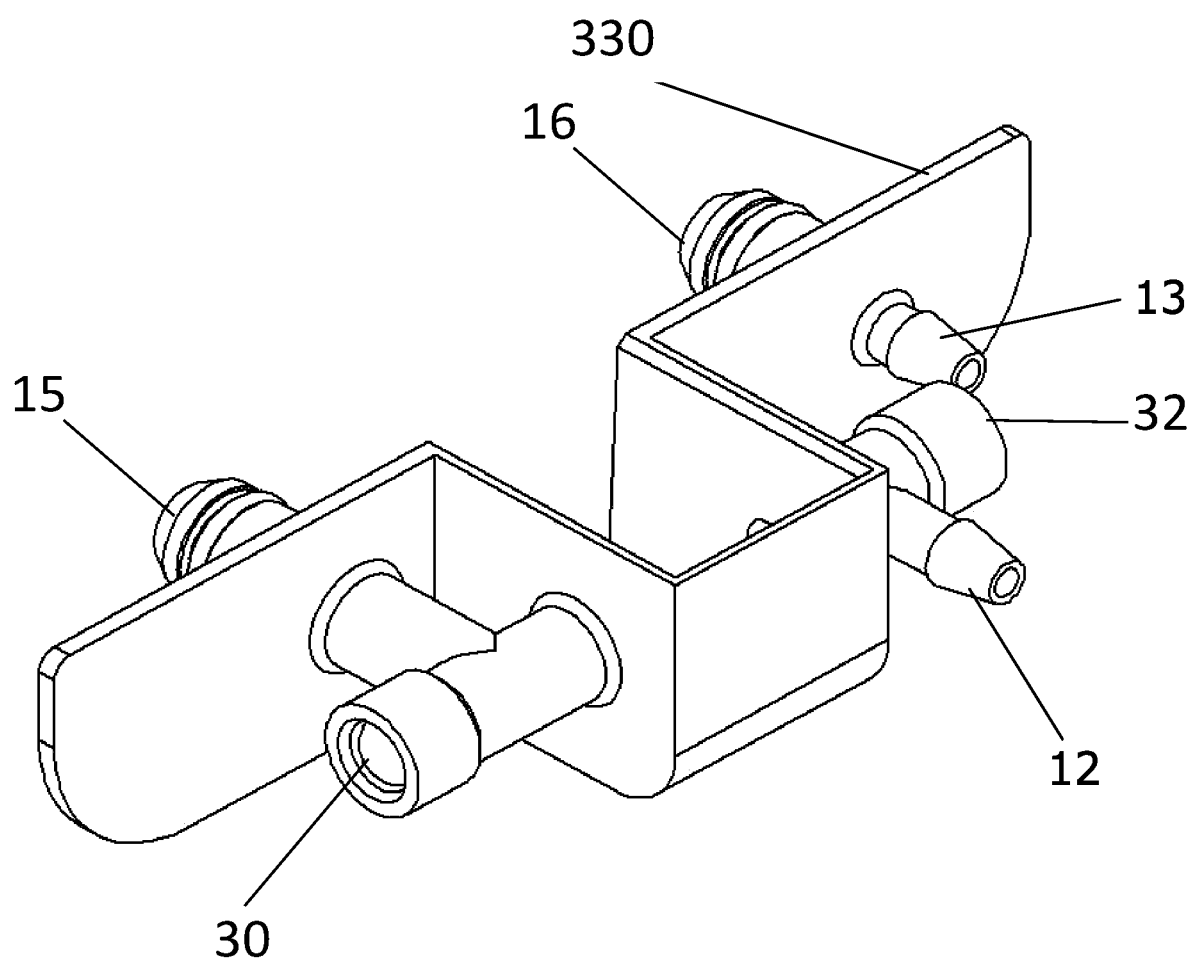
FIG. 4 shows a detailed view of the connector 330 of FIG. 3.

Connecting device 4 comprises a connector (such as the embodiment represented by 330 of FIG. 3 and FIG. 4) so that the connecting device 4 is joined to appropriate components of the system at each of the attachment regions 50, 52 and 53. In some embodiments, the connector is removable. In some embodiments, the connector is removable and replaceable with a second connector. The second connector may be configured to connect to an absorbing dressing, or other fluid retaining wound dressing, to provide a NPWT system as shown in FIG. 2.

An exemplary method for performing NPWT using system 100 comprises drawing exudate from a wound positioned under transfer wound dressing 9 to canister 6 using the pressure difference between the dressing and the canister 6 connected to pump 7. Pump 7 draws air out of canister 6 via the air pathway 55 of connector 4. The exudate is drawn through the fluid pathway 54 of connecting device 4 into canister 6.

Figure 2:
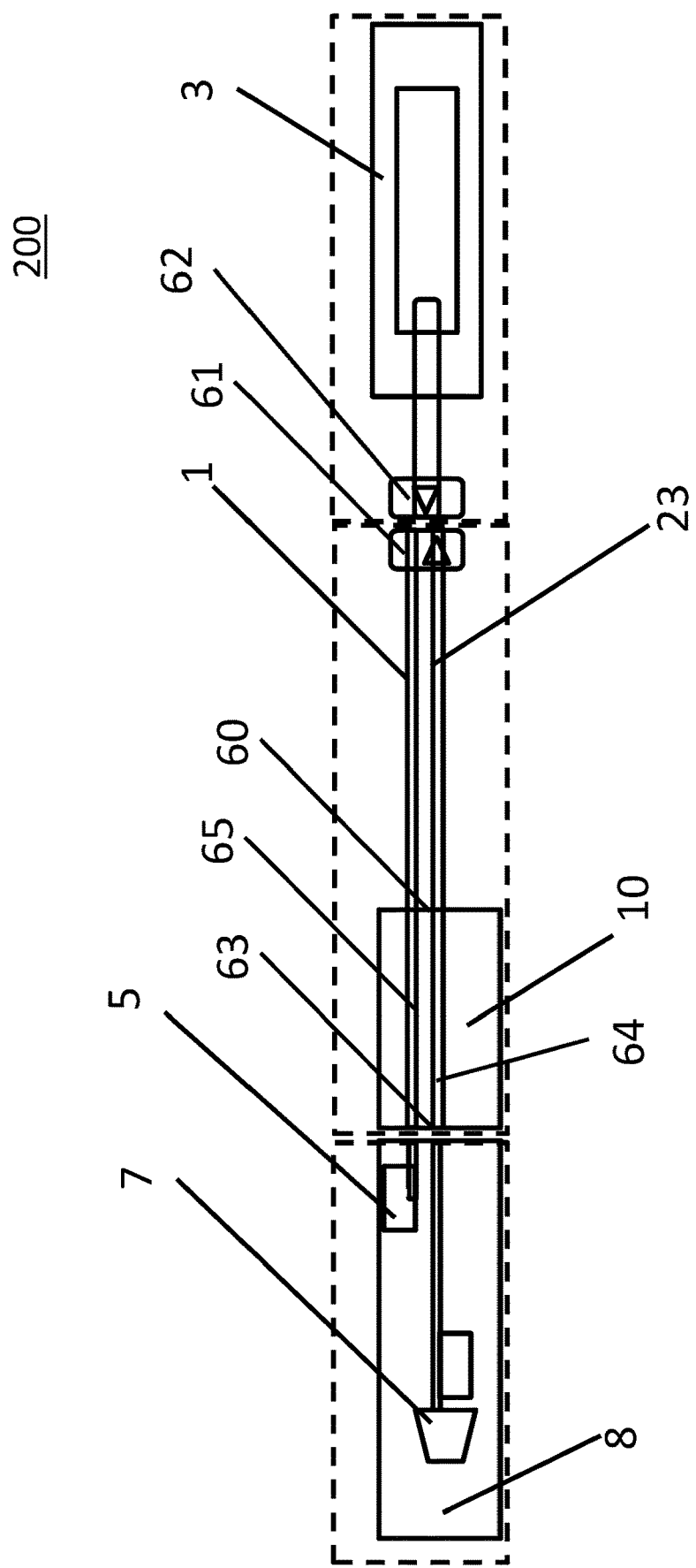
FIG. 2 shows an embodiment of a NPWT system comprising a connecting device 10 attached to an absorbent dressing 3 and a control unit 8.
Figure 6:
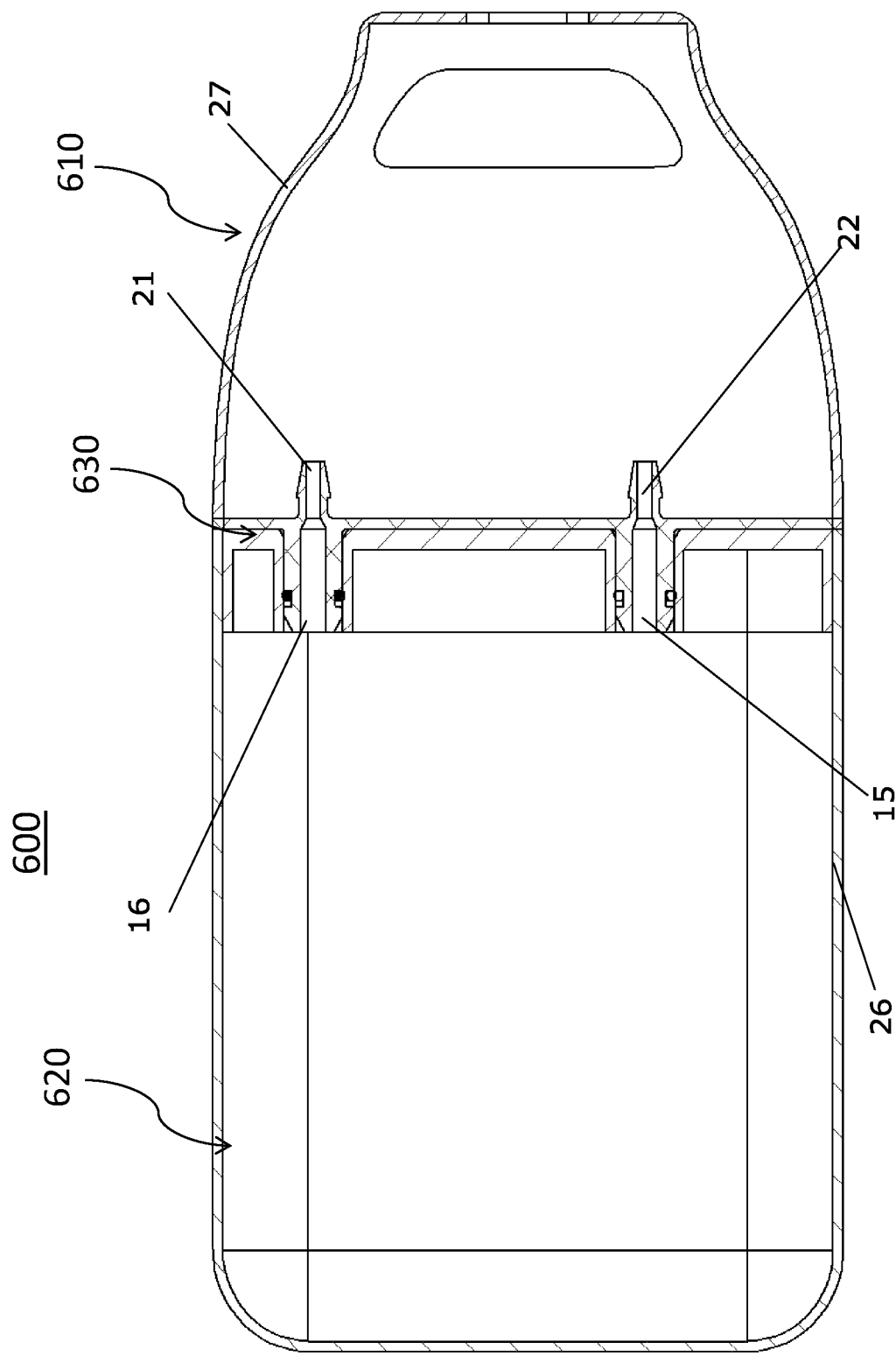
FIG. 6 shows a connecting device 610 joined to a control unit 620 of a NPWT system, where a connector 630 of the connecting device is configured to further join to an absorbent dressing.

An embodiment of a NPWT system 200 comprising a connecting device 10 connected to fluid retention dressing 3 and control unit 8 is shown in FIG. 2. A detailed view of an embodiment of connecting device 10 is shown in FIG. 6 as 610, attached to an embodiment of a control unit 8 shown as 620. Referring to system 200, control unit 8 comprises a pump 7 for drawing exudate from a wound into fluid retention dressing 3 via connecting device 4.

Connecting device 10 is connected to the fluid retention dressing 3 via an air supply tube 23 and a sensing line 1. A first end of air supply tube 23 and a first end of sensing line 1 are connected to connecting device 10 a first attachment portion 60 of the device. The second end of air supply tube 23 and the second end of sensing line 1 form an attachment region 61 that connects air supply tube 23 and sensing line 1 to an outlet 62 of fluid retention dressing 3.

Connecting device 10 is further connected to control unit 8 at a second attachment region 63 of the device. Connecting device 10 comprises an air pathway 64 to allow air to pass between air supply tube 23 and pump 7 of the control unit 8. Connecting device 10 further comprises sensor pathway 65 to connect sensing line 1 and the pressure sensor 5 of the control unit 8.

The connecting device 10 is configured with a connector (such as the embodiment represented by 630 of FIG. 6 and FIG. 7) so that the connecting device 10 is joined to appropriate components of the system at each of the attachment regions 60 and 63. In some embodiments, the connector is removable. In some embodiments, the connector is removable and replaceable with a second connector. The second connector may be configured to connect to a canister to provide a NPWT system configured as shown in FIG. 1.

An exemplary method for performing NPWT using system 200 comprises drawing air out of the wound environment beneath absorbent dressing 3, through the air supply tube 23 and air pathway 64 of connecting device 10, from pump 7. As pump 7 applies this negative pressure to the wound environment, exudates from the wound are drawn into absorbent dressing 3. Sensor 5 senses a pressure state of the wound via sensing line 1, which is connected to sensor 5 via the sensor pathway of connecting device 10.

The systems of FIGS. 1-2 are for illustrative purposes only and it is intended that a NPWT system comprising a connecting device provided herein may comprise additional components and/or lack one or more components shown. For example, one or more sensors within the control unit 8 may not be necessary for the system to function as described. As a further example, the connecting device 4 and/or connecting device 10 may not comprise a sensor pathway. As yet another example, the connecting device 4 and/or connecting device 10 may comprise a power source such as a battery.

In some embodiments, a transfer dressing is a dressing used in NPWT with a canister, where the canister stores the majority, if not all, of exudates drawn from a wound covered with the transfer dressing. In some cases, a transfer dressing further comprises an absorptive property and/or is configured to retain at least a portion of exudates during NPWT. In some cases, a canister and an absorbing dressing, or other fluid retention dressing, are connected via a connector and/or connecting device provided herein. In some such instances, the fluid retention dressing and canister are configured to each retain a portion of exudates drawn from a wound covered with the fluid retention dressing. As such, a fluid retention dressing, such as an absorbent dressing, refers to a dressing used in NPWT to retain some amount of fluid, in a system having or not having a canister. In some cases, the fluid retention dressing or absorbent dressing lacks an absorbing material yet still is configured to retain exudates from a wound during NPWT. As used herein, a fluid retaining source may refer to a fluid retention dressing, such as an absorbing dressing, and/or a canister.

The connecting devices, connectors and systems described herein may be used with any canister available in the art, including the fluid collection apparatus described in U.S. Provisional Application No. 62/360,211, filed 16 July 20127, the contents of which are fully incorporated herein.

Connecting Devices and Connectors

In one aspect of the disclosure, provided herein are connecting devices comprising a housing and a connector, wherein the connector may be configured to connect to fluid retaining source such as a canister and/or an absorbable wound dressing during a NPWT. In some embodiments, two or more connectors having different configurations comprise one universal portion configured to connect to the same universal region of a control unit. As a non-limiting example, a control unit housing a source of negative pressure. In some cases, the universal region of the connector comprises an air outlet fitting and optionally a sensor outlet fitting. In some cases, the control unit comprises a region configured to mate with the universal region of the connector, the control unit comprising a first connection site configured to connect with an air outlet fitting and an optional second connection site configured to connect with a sensor outlet fitting. In some embodiments, the universal region of the connector comprises the air outlet fitting and the sensor outlet fitting, wherein the fittings are spaced between about 4 and about 80 mm apart. The connectors can be placed at the extremes of the width of the mating faces of the device or as close together as their size allows so in some cases they could be placed wider apart or closer together subject to sizing of the device and the connectors. In some cases the connectors can be arranged to be concentric to each other so that one connection is located within the second to provide a convenient form.

In another aspect of the disclosure, provided herein are devices configured to attach with two or more different connectors. As a non-limiting example, the devices comprise a first connection site configured to connect with a first connector or a second connector, where the first connector is configured to attach the device to a first type of fluid retention source and the second connector is configured to attach the device to a second type of fluid retention source. In some cases, the first type of fluid retention source is a canister and the second type of fluid retention source is a dressing, or vice versa. The devices may further comprise a second connection site configured to connect with a sensor fitting of a first connector and a sensor fitting of a second connector, where the first and second connectors are further configured to communicate with a sensing line. As a non-limiting example, devices comprise control units and/or connecting devices as described elsewhere herein.

In some embodiments, provided herein is a device comprising a first connection site configured to connect with an air outlet fitting of a connector, and a second connection site configured to connect with a sensor outlet fitting of the connector; and the connector. In some embodiments, the connector further comprises: an air inlet fitting and an air pathway connecting the air outlet fitting and the air inlet fitting, and a sensor inlet fitting and a sensor pathway connecting the sensor outlet fitting and the sensor inlet fitting. The device connector is selected from: a first connector; and a second connector further comprising a fluid inlet fitting and a fluid outlet fitting connected by a fluid pathway; wherein the first connector and second connector interchangeably connect to the first connection site and second connection site of the device.

In some embodiments, the air outlet fitting or the first connection site comprises a sealing member configured to provide a sealed connection between the air outlet fitting and the first connection site. In some embodiments, the sensor outlet fitting or the second connection site comprises a sealing member configured to provide a sealed connection between the sensor outlet fitting and the second connection site. A non-limiting example of a sealing member is an O-ring.

In some embodiments, the air inlet fitting of the first connector is configured to connect with a first fluid retention source. As a non-limiting example, the first fluid retention source is an absorbent wound dressing comprising an upper adhesive layer, typically with silicone, acrylic or polyurethane adhesive that largely seals the wound from ambient air combined with absorbent materials that are in contact with the wound. Attached to the upper adhesive layer is an air pathway that allows passage of air to the pump and allows measurement of the pressure in the wound. In some cases, the air inlet fitting of the first connector connects to the first fluid retention source via an air supply tube. In some cases, the sensor inlet fitting of the first connector is configured to connect with the first fluid retention source. In some cases, the sensor inlet fitting of the first connector connects to the first fluid retention source via a sensing line.

In some embodiments, the fluid outlet fitting of the second connector is configured to connect with a fluid receiving fitting of a second fluid retention source. As a non-limiting example, the second fluid retention source is a canister. In some cases, the fluid outlet fitting of the second connector or the fluid receiving fitting of the second fluid retention source comprises a sealing member configured to provide a sealed connection between the second connector and the second fluid retention source. In some cases, the fluid inlet fitting of the second connector is configured to connect with a transfer dressing. In some cases, the fluid inlet fitting of the second connector is configured to connect with a fluid retention dressing. For example, the connection between the second connector and transfer dressing or fluid retention dressing is by a fluid supply tube. As a non-limiting example, the transfer dressing comprises an upper adhesive layer, typically with silicone, acrylic or polyurethane adhesive that largely seals the wound from ambient air, combined with wound filling materials such as polyurethane foam that are in contact with the wound. Attached to the upper adhesive layer is a fluid pathway that allows passage of air and exudate to the pump and allows measurement of the pressure in the wound. In some cases, the air inlet fitting of the second connector is configured to connect with an air release fitting of the second fluid retention source. In some cases, the air inlet fitting of the second connector or the air release fitting of the second fluid retention source comprises a sealing member configured to provide a sealed connection between the second connector and the second fluid retention source. A sealing member includes an O-ring. In some embodiments, the sensor inlet fitting of the second connector is configured to connect with the second fluid retention source. In some cases, the sensor inlet fitting of the second connector connects to the second fluid retention source via a sensing line. In some embodiments, the fluid pathway of the second connector is configured to retain a liquid when the fluid outlet fitting of the second connector is not connected to the second fluid retention source. When the second connector is removed from the dressing, the negative pressure within the system will draw fluid away from the open end of the connector. Similarly, if the connector is disconnected from the canister, then the negative pressure in the system will draw fluid away from the open end. In some cases, a non return valve, fluid baffle or absorbent material in the canister will prevent subsequent spillage.

Fittings capable of withstanding pressures used during negative pressure wound therapy are suitable for use in connectors and devices described herein. In some embodiments, the air outlet fitting, sensor outlet fitting, sensor inlet fitting, air inlet fitting of the first connector, air inlet fitting of the second connector, fluid inlet fitting of the second connector, fluid outlet fitting of the second connector, or any combination thereof, is a push to connect fitting, using but not limited to, one a radial seal comprising a mating male and female connector moulded into the components, a mating face seal with a compliant sealing element as a separate component or moulded as part of the main component. In some embodiments, the first connection site comprises a fitting. In some embodiments, the second connection site comprises a fitting. In some embodiments, the first and/or second connection site has a radial seal comprising a mating male and female connector moulded into the components, a mating face seal with a compliant sealing element as a separate component or moulded as part of the main component. Each fitting of the devices and connectors described herein may be female or male. In some cases, the air outlet fitting is a male fitting. In some cases, the sensor outlet fitting is a male fitting. In some cases, the sensor inlet fitting is a male fitting. In some cases, the air inlet fitting of the first connector is a male fitting. In some cases, the air inlet fitting of the second connector is a female fitting. In some cases, the fluid outlet fitting of the second connector is a female fitting. In some cases, the fluid inlet fitting of the second connector is a male fitting. In some cases, the first connection site comprises a female fitting. In some cases, the second connection site comprises a female fitting.

In some embodiments, the first connector, second connector, or both the first connector and second connector are comprised of injection mouldable plastics such as ABS (acrylonitrile-butadiene-styrene), PC (polycarbonate), PC-ABS, PP (polypropylene), HDPE (high-density polyethylene) with sealing components consisting of elastomeric materials such as nitrile or TPE (thermoplastic elastomer) material. In some embodiments, the length of the first connector and the second connector is from about 0.5 cm to about 4 cm, from about 0.5 cm to about 2 cm, for example, about 1 cm. In some embodiments, the length of the air pathway between the air inlet and air outlet is between about 0.5 cm and about 2 cm. In some embodiments, the length of the sensor pathway between the sensor inlet and sensor outlet is between about 0.5 cm and about 2 cm. In some embodiments, the diameter of the air pathway is between about 0.5 mm and about 5 mm, between about 0.5 mm and about 3 mm, between about 1 mm and about 3 mm, or about 2 mm. In some embodiments, the diameter of the sensor pathway is between about 0.5 mm and about 5 mm, between about 0.5 mm and about 3 mm, between about 1 mm and about 3 mm, or about 2 mm.

In some embodiments, the first connection site and the second connection site are positioned on a first side of the device. In some cases, the shortest distance between the center of the first connection site and the center of the second connection site is between about 1 mm and about 20 mm, between about 1 mm and about 10 mm, or about 1 mm, 2 mm, 5 mm, or 7 mm.

In some embodiments, the device comprises a first compartment and a second compartment connected by the first connector or the second connector. In some cases, the first compartment comprises the first connection site and the second connection site, and the first connection site is connected to a source of negative pressure. In a non-limiting example, the first compartment is a control unit comprising the source of negative pressure. An example of a source of negative pressure is a diaphragm pump driven by a rotary DC brushed motor. Alternatively a brushless DC motor is used to drive the diaphragm pump or a linear actuator such as a voice coil actuator directly drives a diaphragm. In some embodiments, the second connection site is configured to be in fluid communication with a pressure sensor. In some cases, the first compartment comprises the pressure sensor, such as a miniature (e.g., less than 1 cm$^3$ size) pressure sensor by Omron, part number SMPP03, range +/−50 kPa, Honeywell; part number ABP L LN N 250 MD A A 3 range +/−250 mbar; and by NXP, part number MPXV7025DP with range −25 kPa to 25 kPa. In some embodiments, the second compartment comprises a power source. In some cases where the device comprises the first connector, the power source is configured to power a source of negative pressure from about 24 hours to about 30 days. Typically a CR123a lithium manganese primary cell will provide sufficient energy for 4 to 8 days of NPWT therapy depending on a number of factors such as the exudate rate of the wound and air leak rate of the applied dressing. In some cases where the device comprises the second connector, the power source is configured to power a source of negative pressure from about 24 hours to about 60 days. Similarly, a CR123a lithium manganese primary cell will provide sufficient energy for 4 to 8 days of NPWT therapy depending on a number of factors such as the exudate rate of the wound and air leak rate of the applied dressing. A non-limiting example of a power source is a battery. Another non-limiting example of a power source for devices connected to either first or second connectors is a rechargeable battery. The rechargeable battery is useful for maintaining power to the device without subjected the patient to an inconvenience of being tethered during use. In some embodiments, the power source is removable from the second compartment. In some embodiments, the power source is replaceable. The first compartment may further comprise one or more additional features, for example, a controller for controlling operation of the source of negative pressure. In some embodiments, the first compartment, second compartment, or both compartments are comprised of ABS, PC, HDPE, PP, PC-ABS material in thicknesses of between 0.5 mm and 3 mm, typically about 1.5 mm, to provide resistance to negative pressure and mechanical loads anticipated in use.

In some embodiments, the air outlet fitting comprises an electrical contact. This electrical contact may provide an electrical connection within the device when the air outlet fitting is connected to the first connection site. In some cases where the first connection device is part of a control unit housing a source of negative pressure and the air outlet fitting is part of a second compartment comprising a power source, the power source provides a power to operate the source of negative pressure through the electrical connection between the second compartment and control unit.

Figure 8:
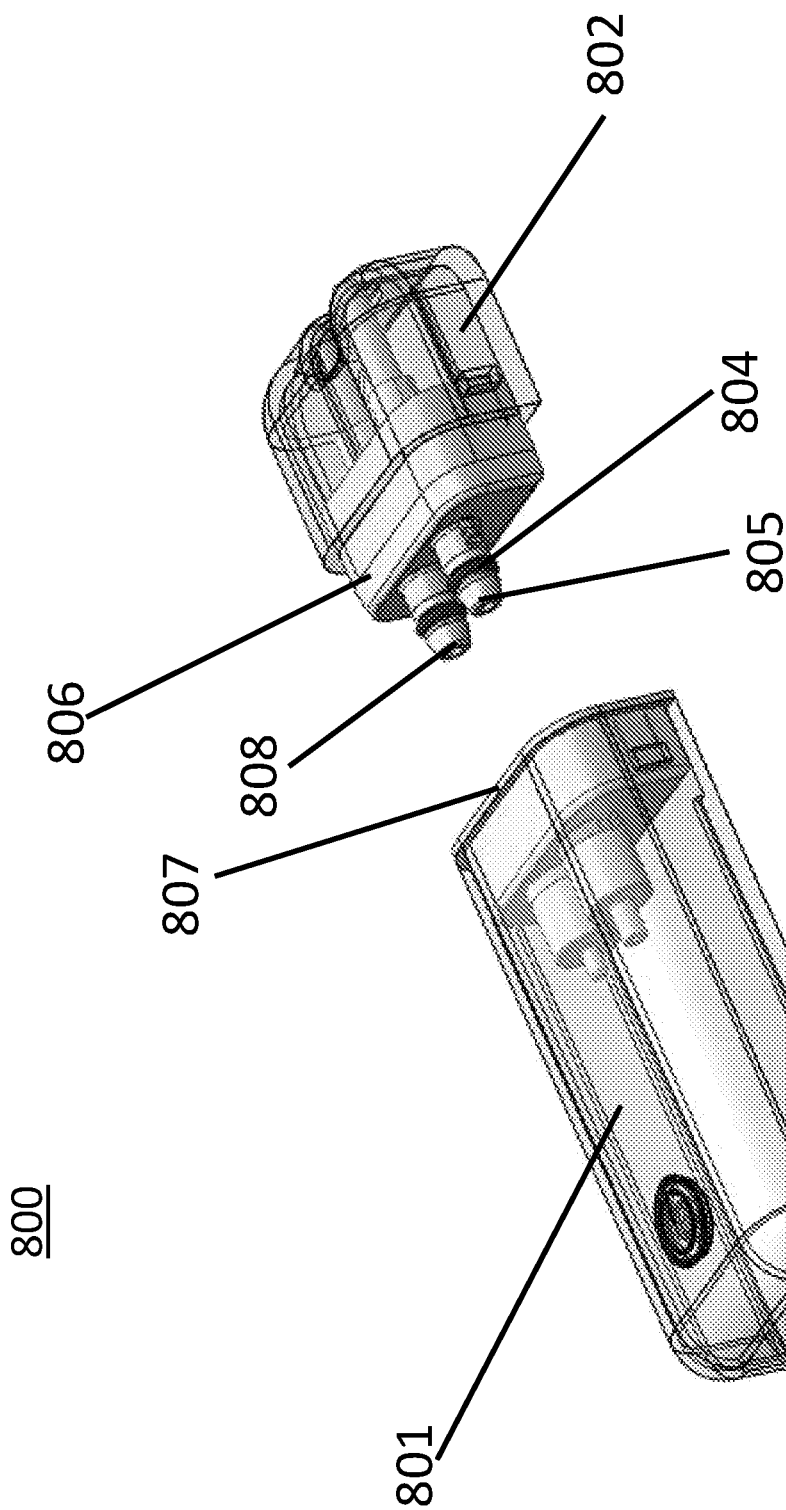
FIG. 8 shows a control unit 801, and a connecting device 802 comprising a connector 806 configured to join with the control unit 801.

An exemplary device for use in negative pressure wound therapy is shown in FIG. 8. Device 800 comprises a control unit 801 and a connecting device 802. Control unit 801 comprises a source of negative pressure (not shown), and a first connection site and second connection site (collectively, 807). Connecting device 802 comprises connector 806, connector 806 comprising an air outlet fitting 805 and a sensor outlet fitting 808, which form an attachment point for connecting device 802 with control unit 801. Located at the air outlet fitting is electrical contact 804. When the connecting device 802 and control unit 801 are connected through mating between air outlet fitting 805 and the first connection site, and mating between sensor outlet fitting 808 and the second connection site, a power source positioned within connecting device 802 provides power to operate the negative pressure source within control unit 801. Control unit 801 optionally further comprises one or more of a control circuit, pressure sensor(s), and elements that comprise a user interface such as lights, switches, and other display elements. When this device is used during negative pressure wound therapies, connecting device 802 may be replaced as a natural part of replacing the dressing on the patient. In addition or alternatively, the connecting device 802 is replaced when additional power is required to operate the negative pressure source and/or one or more features of the control unit.

Figure 9A:
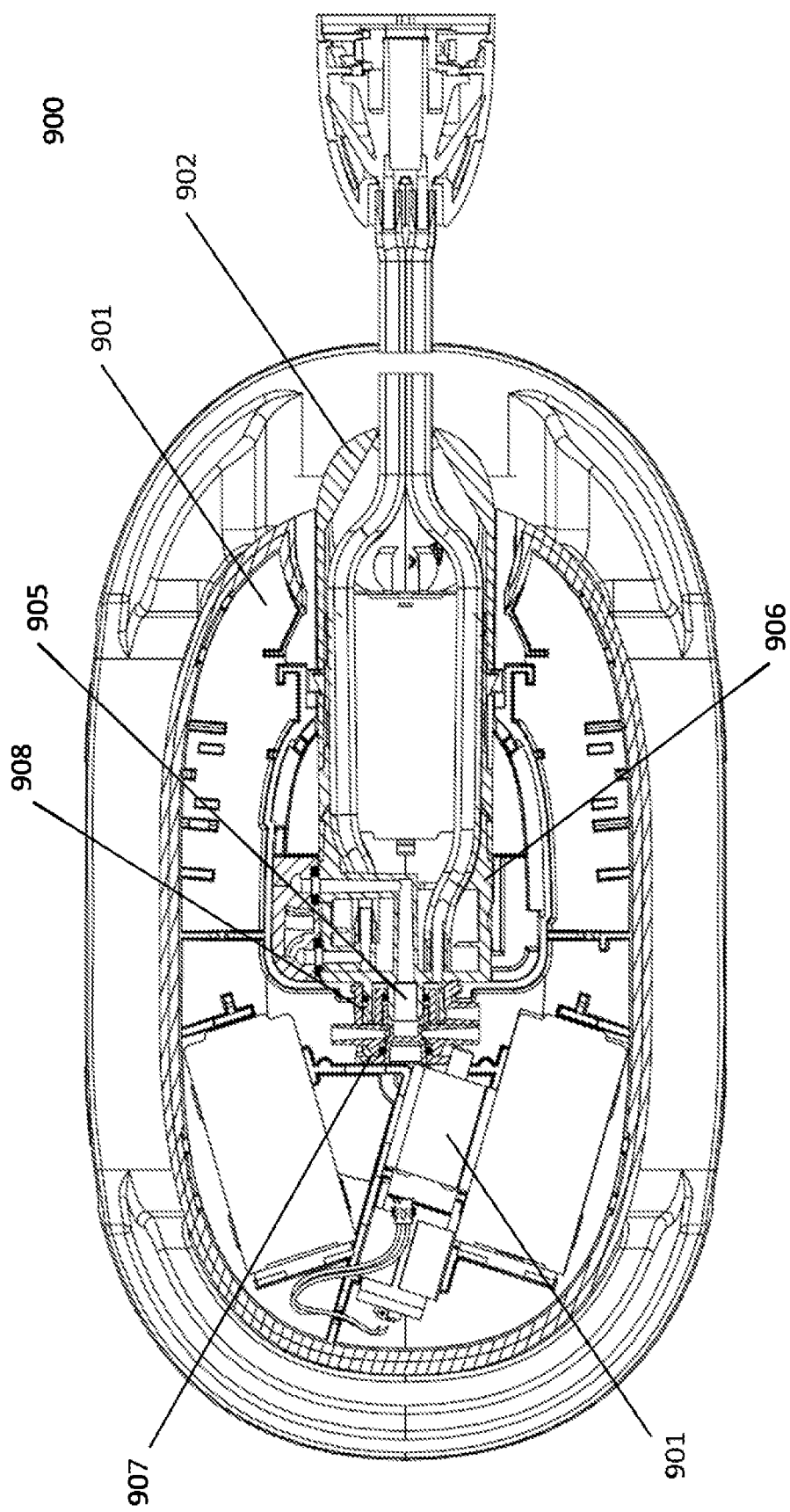
FIG. 9A shows an overview of the fluid connections for an exemplary embodiment of a connecting device, including connections to a canister.
Figure 9B:
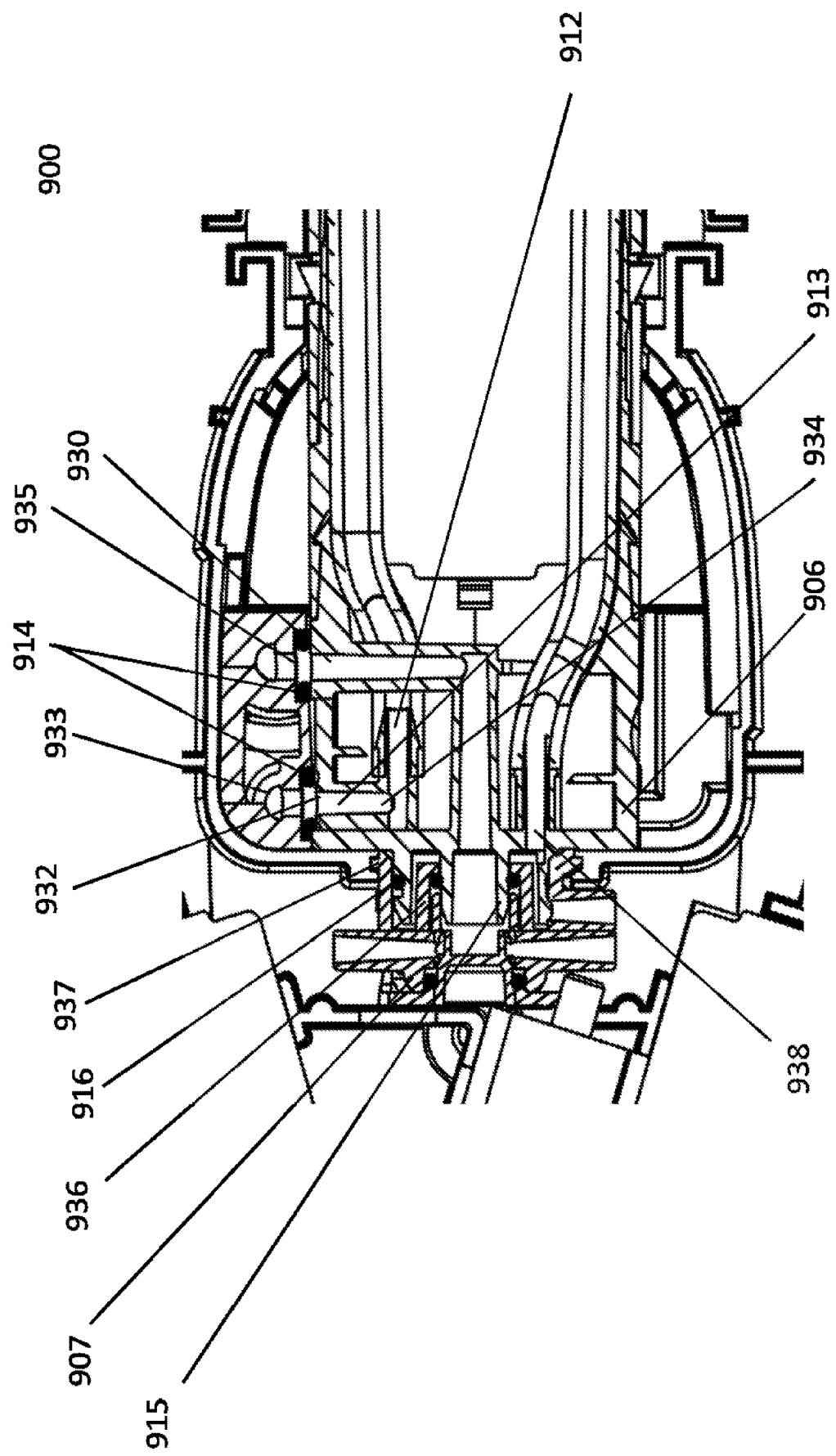
FIG. 9B shows a more detailed view of the fluid connections of the exemplary embodiment shown in FIG. 9A.

A second exemplary device is shown in cross section in FIGS. 9A and 9B. Device 900 comprises a control unit 901 and a connecting device 902. Control unit 901 comprises a source of negative pressure 910 (shown without tube connection to connection site 907 for clarity), and a first connection site and second connection site (collectively, 907). Connecting device 902 comprises connector 906, which comprises an air outlet fitting 905 and a sensor outlet fitting 908, which form an attachment point for connecting device 902 with control unit 901.

Connecting device 902 has a number of electrical contacts. Exemplary embodiments of the contacts are shown in the connecting devices of FIGS. 12 and 13 as 1204 and 1304, respectively. When the connecting device 902 and control unit 901 are connected through mating between air outlet fitting 905 and the first connection site, and mating between sensor outlet fitting 908 and the second connection site, a power source positioned within connecting device 902 provides power to operate the negative pressure source within control unit 901. Control unit 901 optionally further comprises one or more of a control circuit, pressure sensor(s), and elements that comprise a user interface such as lights, switches, and other display elements. When this device is used during negative pressure wound therapies, connecting device 902 may be replaced as a natural part of replacing the dressing on the patient. In addition, or alternatively, the connecting device 902 is replaced when additional power is required to operate the negative pressure source and/or one or more features of the control unit.

Canister Connectors

In another aspect of the disclosure, provided herein are connectors for use in NPWT with a canister, the connectors comprising a fluid inlet fitting connected by a fluid pathway to a fluid outlet fitting, and an air inlet fitting connected by an air pathway to an air outlet fitting; wherein the fluid outlet fitting is configured to be in fluid communication with the air inlet fitting upon joining the fluid outlet fitting and the air inlet fitting to the canister. In some embodiments, the fluid outlet fitting is configured to connect with a fluid receiving fitting of the canister. In some cases, the fluid outlet fitting of the connector or the fluid receiving fitting of the canister comprises a sealing member configured to provide a sealed connection between the connector and the canister. In some embodiments, the air inlet fitting is configured to connect with an air release fitting of the canister. In some cases, the air inlet fitting of the connector or the fluid receiving fitting of the canister comprises a sealing member configured to provide a sealed connection between the connector and the canister. In some embodiments, the fluid inlet fitting is configured to connect with a transfer dressing, for example, via a fluid supply tube. In some embodiments, the fluid inlet fitting is configured to connect with a fluid retention dressing, for example, via a fluid supply tube. In some embodiments, the air outlet fitting is configured to be in fluid communication with a source of negative pressure upon connection of the air outlet fitting to a connection site of the negative pressure source. In some cases, the air outlet portion of the connector or the connection site of the negative pressure source comprises a sealing member configured to provide a sealed connection between the connector and the negative pressure source. A non-limiting example of a sealing member is an O-ring or other sealing member such as a gasket of compliant material or a moulded seal such as a TPE surface. A non-limiting example of a source of negative pressure is a diaphragm pump driven by a rotary DC brushed motor. Alternatively, a brushless DC motor is used to drive the diaphragm pump or a linear actuator such as a voice coil actuator directly drives a diaphragm. In some embodiments, the connector further comprises a sensor inlet fitting connected to a sensor outlet fitting by a sensor pathway.

In some embodiments, the fluid inlet fitting, fluid outlet fitting, air inlet fitting, air outlet fitting, or a combination thereof, is a push to connect fitting as described herein. In some cases, the fluid inlet fitting is a male fitting. In some cases, the fluid outlet fitting is a female fitting. In some cases, the air inlet fitting is a female fitting. In some cases, the air outlet fitting is a male fitting.

In some embodiments, the fluid pathway connecting the fluid inlet fitting and the fluid outlet pathway is configured to retain a liquid when the fluid outlet fitting and the air inlet fitting are not joined to the canister.

In some embodiments, the connector is comprised of a plastic mouldable component, for example, comprising ABS, PC, PC-ABS, HDPE, and/or PP combined with an elastomeric element such as nitrile, silicone, and/or TPE. In some embodiments, the length of the connector is between about 4 and about 20 mm, using but not limited to, a radial seal comprising a mating male and female connector moulded into the components, a mating face seal with a compliant sealing element as a separate component or moulded as part of the main component. In some embodiments, the width of the connector is between about 5 mm and about 30 mm, between about 10 mm and about 20 mm, or about 10 mm, 12 mm, 15 mm, 17 mm, or 20 mm. In some embodiments, the length of the air pathway is between about 0.5 cm and about 2 cm. In some embodiments, the length of the fluid pathway is between about 0.5 cm and about 2 cm. In some embodiments, the diameter of the air pathway is between about 0.5 mm and about 5 mm, or about 1.5 mm. In some embodiments, the diameter of the fluid pathway is between about 1 mm and about 6 mm, or about 2 mm.

Figure 11:
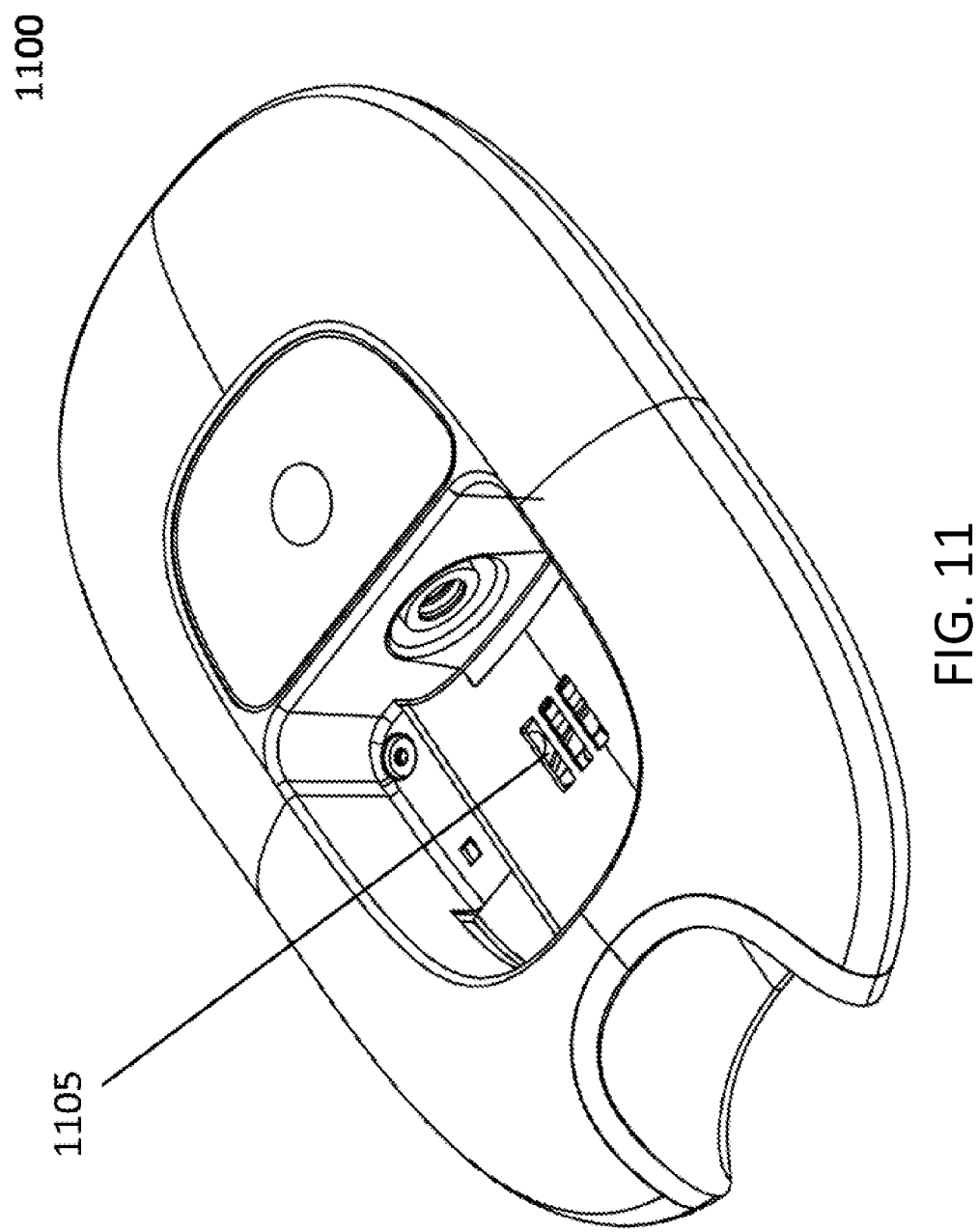
FIG. 11 shows the underside of an exemplary embodiment of a control unit and its electrical connections.
Figure 12:
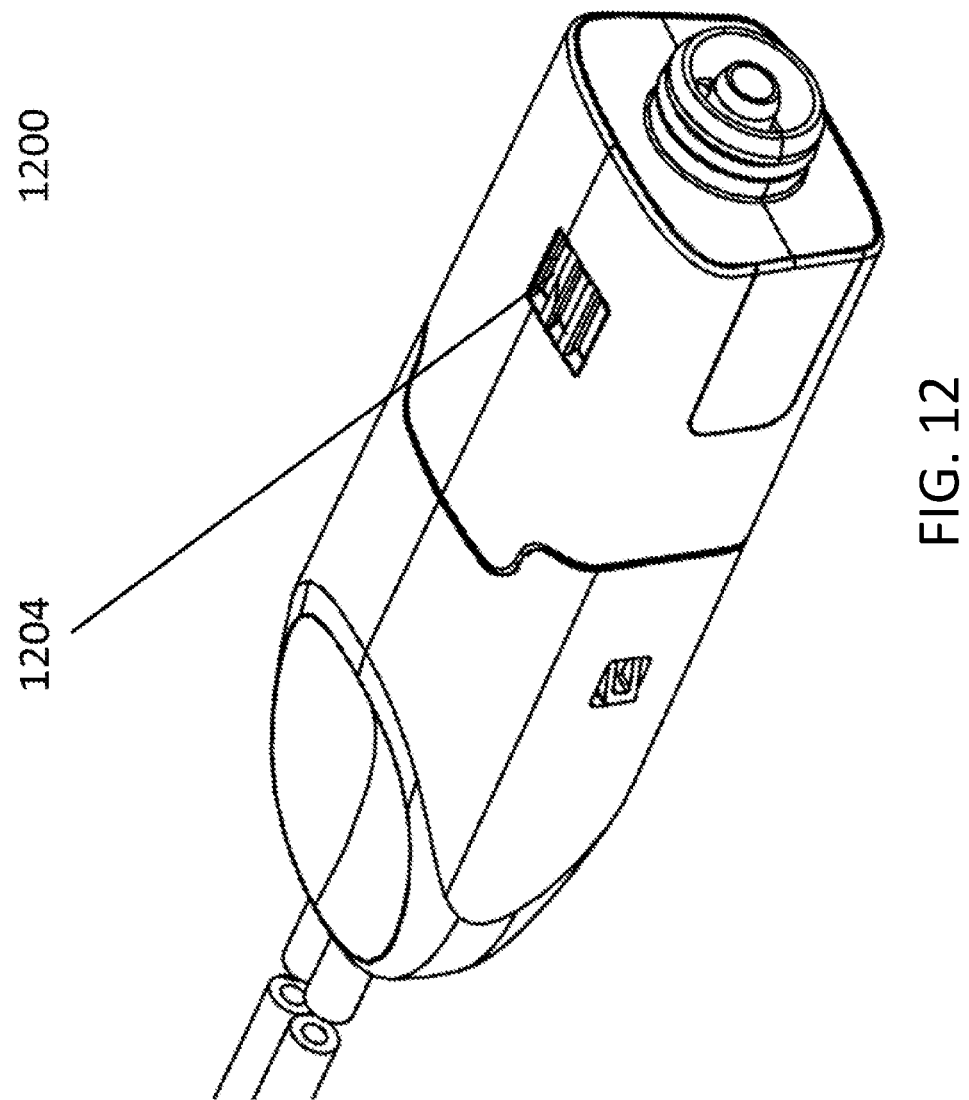
FIG. 12 shows an exemplary embodiment of a connection device for use with an absorbing dressing and its electrical connections.
Figure 13:
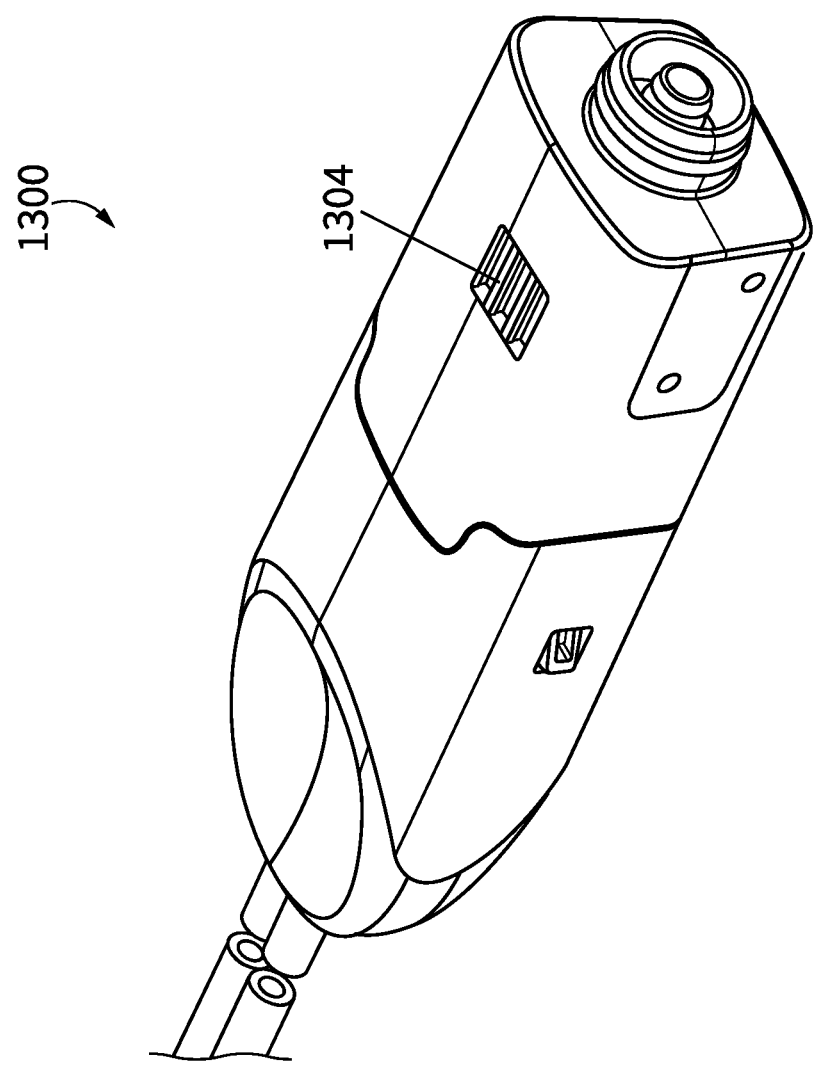
FIG. 13 shows an exemplary embodiment of a connection device for use with a transfer dressing and canister, with its electrical connections.

In some embodiments, the air outlet fitting comprises an electrical contact. The electrical contact may be connected to a power source, where the power source and the connector are part of a connecting device, the connecting device further comprising a power source. In other embodiments, electrical contacts are incorporated in the body of the connecting device. FIG. 12 and FIG. 13 show these contacts as 1204 and 1304 respectively, arranged to make electrical contact to the control unit via contacts incorporated into the body of the control unit shown as 1105 in FIG. 11. In some cases, the power source is configured to power a source of negative pressure from about 24 hours to about 60 days. A non-limiting example of a power source is a battery. In some embodiments, the power source is removable from the second compartment. In some cases, the power source is replaceable.

Further provided herein are devices and systems comprising a connector for use with a canister as described herein, and the canister. In some embodiments, provided herein are devices and systems comprising the connector and a source of negative pressure. In some embodiments, provided herein are devices and systems comprising the connector and a transfer dressing. In some embodiments, provided herein are devices and systems comprising the connector and a fluid retention dressing.

In certain embodiments, a connector for use in NPWT with a canister comprises a fluid inlet fitting connected by a fluid pathway to a fluid outlet fitting, and an air inlet fitting connected by an air pathway to an air outlet fitting; wherein the fluid outlet fitting and the air inlet fitting are in fluid communication when each fitting is connected to the canister; wherein the fluid inlet fitting is configured to communicate with a transfer dressing or fluid retention dressing; and wherein the air outlet fitting is configured to communicate with a negative pressure source, the negative pressure source supplying negative pressure to the site of the transfer or fluid retention dressing when the negative pressure source, connector, canister, and transfer or fluid retention dressing are connected. In this configuration, fluid is drawn from a wound site covered with the transfer or fluid retention dressing, is passed into the connector via the fluid inlet, through the fluid outlet and into the canister, where liquid is retained. Air is then passed from the canister, through the air inlet, and out of the air outlet of the connector to a connected negative pressure source. In some embodiments, the negative pressure source is a diaphragm pump. In many embodiments, the connector and device connected thereto have a small footprint such that the device facilitates use by a patient who is mobile and/or without necessitating a clinical environment or bulky equipment. As a non-limiting example, a connector for use with a canister has a length of about 0.5 cm to about 2 cm, or about 1 cm, and a width of about 1 cm to about 2 cm. Similarly, the length of the fluid pathway is about 0.5 cm to about 2 cm, with a diameter of about 0.5 mm to about 2 mm. In certain embodiments, a connector for use with a canister is part of a device housing a power source, such as a battery, such that upon connecting the device with the negative pressure source, the power source supplies power to the negative pressure source.

A non-limiting example of a device comprising a connector for use with a canister is shown in FIG. 3. Device 300 comprises a control unit 320 connected to a connecting device 310 by connector 330 (represented by hash marks). Connecting device 310 comprises a housing 10 and connector 330. Control unit 320 comprises a housing 26 comprising a first connection port and a second connection port, each port configured to connect to fittings of connector 330. Connector 330 comprises an air outlet fitting 15 configured to connect with the first connection port of control unit 320, and a sensor outlet fitting 16 configured to connect with the second connection port of control unit 320. Air outlet fitting 15 is connected to air inlet fitting 30 by air pathway 11 in connector 330. Air inlet fitting 30 is configured to be in communication with fluid outlet fitting 32 upon connection of 30 and 32 to the canister. Fluid outlet fitting 32 is connected with fluid inlet fitting 12 by fluid pathway 33. Air inlet fitting 30 and fluid outlet fitting 32 each comprise a seal 14, to provide a sealed connection with the canister. Sensor outlet fitting 16 is connected to sensor inlet fitting 13 by sensor pathway 31 in connector 330. A close-up view of connector 330 showing fluid inlet fitting 12, fluid outlet fitting 32, air inlet fitting 30, air outlet fitting 15, sensor inlet fitting 13, and sensor outlet fitting 16, is provided by FIG. 4.

Figure 5:
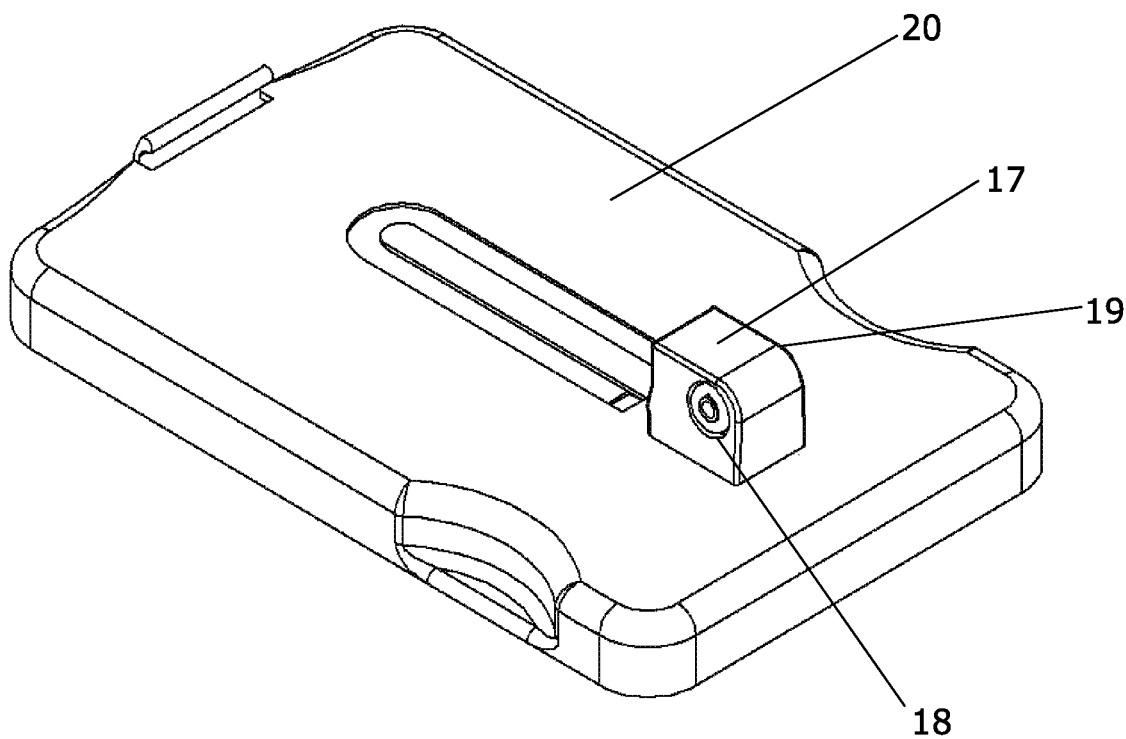
FIG. 5 shows a top view of a canister header comprising a port configured to engage with the connector 330 of FIGS. 3 and 4.

In some configurations, device 300 is configured in a negative pressure wound therapy system as generally shown in FIG. 1. In this case, control unit 320 of FIG. 3 corresponds with control unit 8 of FIG. 1. Connector 330 is connected to control unit 8 by connections between air outlet fitting 15 and sensor outlet fitting 16, where air outlet fitting 15 communicates with pump 7 and sensor outlet fitting 16 communicates with sensor 5. Air inlet fitting 30 and fluid outlet fitting 32 connect to canister 6. Fluid inlet fitting 12 connects to dressing 9 via fluid supply tube 2. Sensor inlet fitting 13 connects to dressing 9 via sensing line 1. An example of a canister header 20 connected to a connector such as connector 330 is shown in FIG. 5. Canister header 20 comprises a port 17 comprising a fluid receiving fitting 19 and an air release fitting 18. Fluid receiving fitting 19 is configured to mate with fluid outlet fitting 32 while air release fitting 18 is configured to mate with air inlet fitting 30.

A second non-limiting example of a device comprising a connector for use with a canister is shown in FIG. 9B. Device 900 comprises a control unit 901 connected to a connecting device 902 by connector 906. Control unit 901 comprises a connection site 907 comprising a first connection port and a second connection port arranged substantially concentrically, each port configured to connect to fittings of connector 906. Connector 906 comprises an air outlet fitting 915 configured to connect with the first connection port 936 of control unit, and a sensor outlet fitting 916 configured to connect with the second connection port 934 of the control unit 901. Fluid Outlet fitting 913 of the connector 906 is configured to be communication with fluid inlet port 932 of the canister and air inlet fitting 930 is configures to be in communication with air outlet port 935 of the canister. Fluid outlet fitting 913 is connected with fluid inlet fitting 912 by fluid pathway 934. Fluid inlet port 932 and air outlet port 935 each comprise a seal 914, to provide a sealed connection with the connector 906. Sensor outlet fitting 916 is connected to second connection port 937 by sensor pathway 938 in connector 906.

Figure 10:
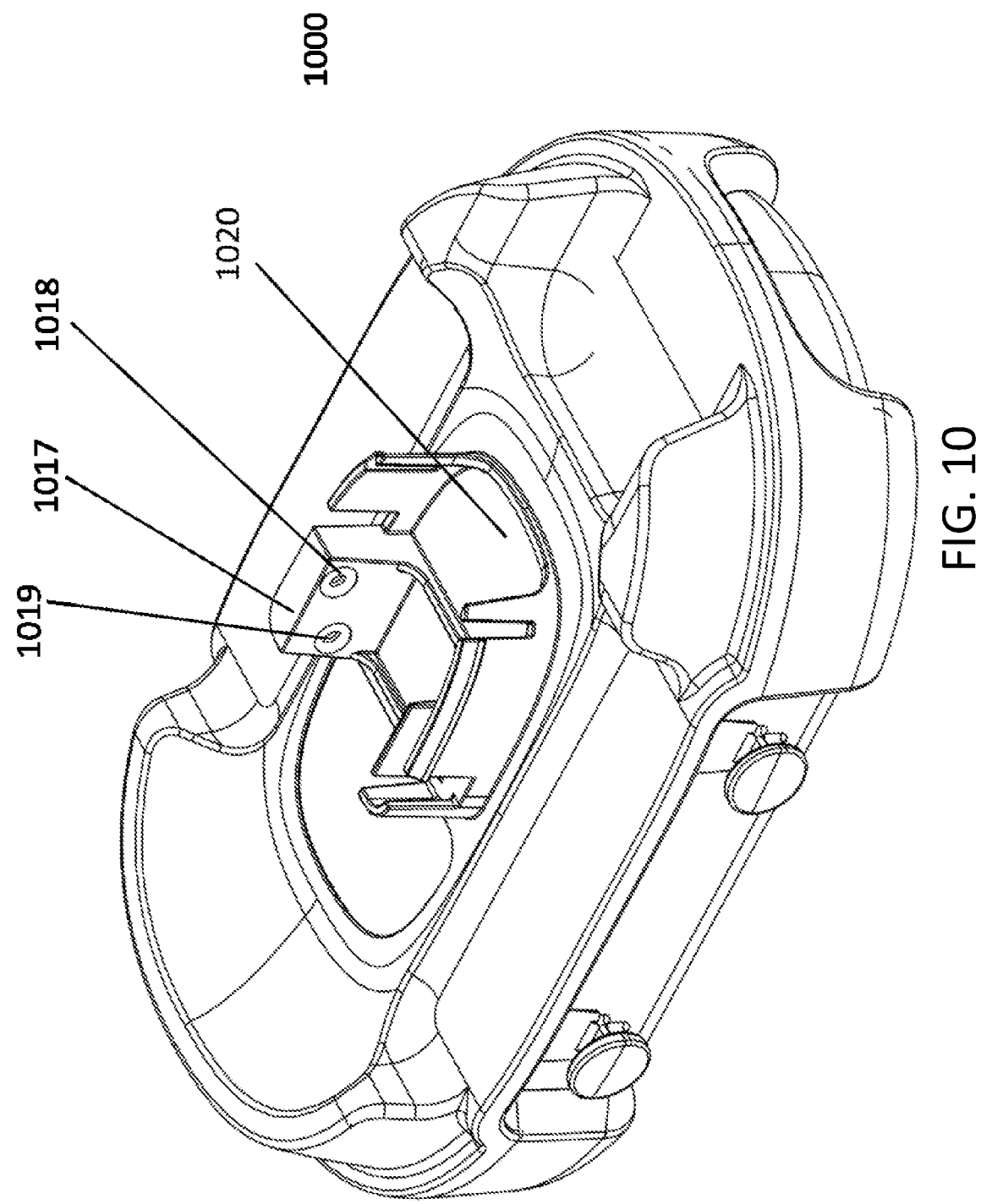
FIG. 10 shows an exemplary embodiment of a canister comprising a port configured to connector to an embodiment of a connector described herein.

An example of a canister header 1020 connected to a connector such as connector 906 is shown in FIG. 10. Canister header 1020 comprises a port 1017 comprising a fluid receiving fitting 1019 and an air release fitting 1018. Fluid receiving fitting 1019 is configured to mate with fluid outlet fitting 932 while air release fitting 1018 is configured to mate with air inlet fitting 930.

Retention Dressing Connectors

In another aspect of the disclosure, provided herein are connectors for use in a canister-free NPWT with a fluid retention dressing, the connector comprising an air inlet fitting connected by an air pathway to an air outlet fitting; wherein air inlet fitting is configured to connect with the fluid retention dressing and the air outlet fitting is configured to connect with a source of negative pressure such that a negative pressure applied from the source of negative pressure is received by the fluid retention dressing. In some embodiments, the connector further comprises a sensor inlet fitting connected by a sensor pathway to a sensor outlet fitting. In some cases, the sensor inlet fitting is configured to connect with the fluid retention dressing. In some cases, the sensor outlet fitting is configured to connect with a pressure sensor. In some embodiments, the pressure sensor and source of negative pressure are housed in a control unit.

In some embodiments, the air inlet fitting or the air outlet fitting is a push to connect fitting, using, but not limited to, a radial seal comprising a mating male and female connector moulded into the components, a mating face seal with a compliant sealing element as a separate component or moulded as part of the main component. In some cases, the air inlet fitting is a male fitting. In some cases, the air outlet fitting is a male fitting.

In some embodiments, the length of the air pathway is between about 0.5 cm and about 2 cm. In some embodiments, the length of the connector is between about 4 mm and about 20 mm. In some embodiments, the width of the connector is between about 10 mm and about 80 mm, between about 10 mm and about 40 mm, or between about 10 mm and about 30 mm, for example, about 10 mm, 12 mm, 15 mm, 17 mm or 20 mm. In some embodiments, the diameter of the air pathway is between about 1 mm and about 5 mm, for example, about 2 mm. In some embodiments, the connector comprises ABS, PC, PC-ABS, PP, HDPE or similar injection mouldable material. In some cases, the connector is comprised of ABS In some embodiments, the air outlet fitting comprises an electrical contact. The electrical contact may be connected to a power source, where the power source and the connector are part of a connecting device, the connecting device further comprising a power source. In some cases, the power source is configured to power a source of negative pressure from about 24 hours to about 30 days. A non-limiting example of a power source is a battery. In some embodiments, the power source is removable from the second compartment. In some cases, the power source is replaceable.

Further provided herein are devices and systems comprising a connector for use with a fluid retention dressing as described herein, and the fluid retention dressing. In some embodiments, the fluid retention dressing comprises a backing configured to create an enclosure between an interior surface of the backing and a wound for retaining fluid drawn from the wound during application of negative pressure. The enclosure may comprise an absorbent material. In some cases, the fluid retention dressing is an absorbing dressing. In some embodiments, provided herein are devices and systems comprising the connector and a source of negative pressure.

In certain embodiments, a connector for use in NPWT with a fluid retaining dressing (or absorbent dressing) comprises an air inlet fitting connected by an air pathway to an air outlet fitting, wherein air inlet fitting is configured to connect with the fluid retention dressing and the air outlet fitting is configured to connect with a source of negative pressure such that a negative pressure applied from the source of negative pressure is received by the fluid retention dressing when the negative pressure source, connector, and dressing are connected. In this configuration, fluid is drawn from a wound site into the dressing, where it is retained. Air is then passed from the dressing, through the air inlet and out of the air outlet of the connector to the connected negative pressure source. In some embodiments, the negative pressure source is a diaphragm pump. In many embodiments, the connector and device connected thereto have a small footprint such that the device facilitates use by a patient who is mobile and/or without necessitating a clinical environment or bulky equipment. As a non-limiting example, a connector for use with a fluid retaining dressing has a length of about 0.5 cm to about 2 cm, or about 1 cm, and a width of about 1 cm to about 2 cm. Similarly, the length of the fluid pathway is about 0.5 cm to about 2 cm, with a diameter of about 0.5 mm to about 2 mm. In certain embodiments, a connector for use with a fluid retaining dressing is part of a device housing a power source, such as a battery, such that upon connecting the device with the negative pressure source, the power source supplies power to the negative pressure source.

A non-limiting example of a device comprising a connector for use with a fluid retention dressing is shown in FIG. 6. Device 600 comprises a control unit 620 connected to a connecting device 610 by connector 630 (represented by hash marks). Connecting device 610 comprises a housing 27 and connector 630. Control unit 620 comprises a housing 26 comprising a first connection port and a second connection port, each port configured to connect to fittings of connector 630. Connector 630 comprises an air outlet fitting 15 configured to connect with the first connection port of control unit 620, and a sensor outlet fitting 16 configured to connect with the second connection port of control unit 620. Air outlet fitting 15 is connected to air inlet fitting 22 by an air pathway in connector 630. Sensor outlet fitting 16 is connected to sensor inlet fitting 21 by a sensor pathway in connector 630. A close-up view of connector 630 showing air inlet fitting 21, air outlet fitting 15, sensor inlet fitting 22, and sensor outlet fitting 16, is provided by FIG. 7.

In some configurations, device 600 is configured in a negative pressure wound therapy system as generally shown in FIG. 2. In this case, control unit 620 of FIG. 6 corresponds with control unit 8 of FIG. 2. Connector 630 is connected to control unit 8 by connections between air outlet fitting 15 and sensor outlet fitting 16, where air outlet fitting 15 communicates with pump 7 and sensor outlet fitting 16 communicates with sensor 5. Air inlet fitting 21 connects to dressing 3 by air supply tube 23 and sensor inlet fitting 22 connect to dressing 3 by sensing line 1.

In some embodiments, control unit 320 of FIG. 3 is configured to receive connector 630 of FIG. 6. In some embodiments, control unit 620 of FIG. 6 is configured to receive connector 330 of FIG. 3. As a non-limiting example, the control units 8 of FIGS. 1-2 are substantially the same. In this system, when a patient requires a NPWT with a canister, connecting device 310 comprising connector 330 is connected to a control unit 8. Similarly, when a patient requires a NPWT with a fluid retaining dressing and no canister, connecting device 610 comprising connector 630 is connected to control unit 8. The combination of different connectors with the same control unit and source of negative pressure offers flexibility during NPWT.

Figure 14:
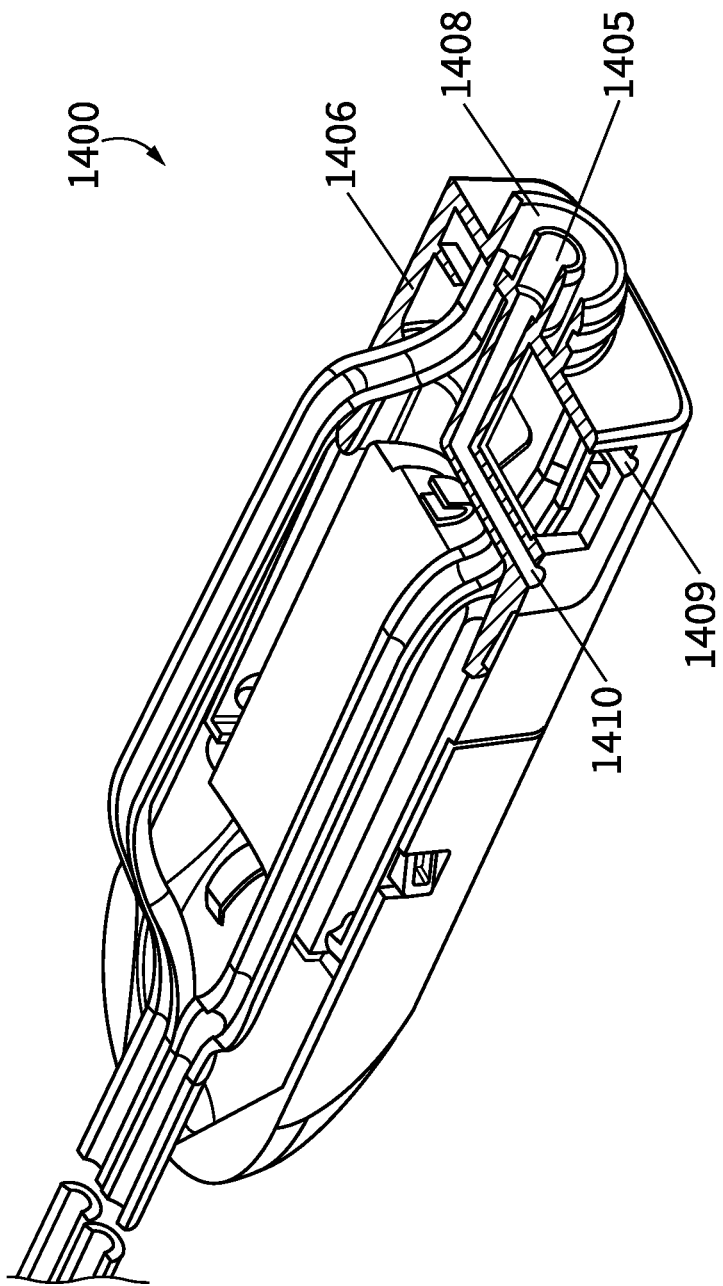
FIG. 14 shows a cutaway view of an exemplary embodiment of connection device for use with a transfer dressing and its fluid connections.

A connector as generally embodied in FIGS. 9A and 9B is shown in FIG. 14. FIG. 14 shows a connecting device 1400 comprising a connector 1406 comprising an air outlet fitting 1405 together with the sensor outlet fitting 1408. The fluid outlet fitting 1409 connects to the canister and the air outlet fitting 1410 correspond to 932 and 930 respectively in FIG. 9B. The connector of FIGS. 14 and 15 are indicated by hash marks.

Figure 15:
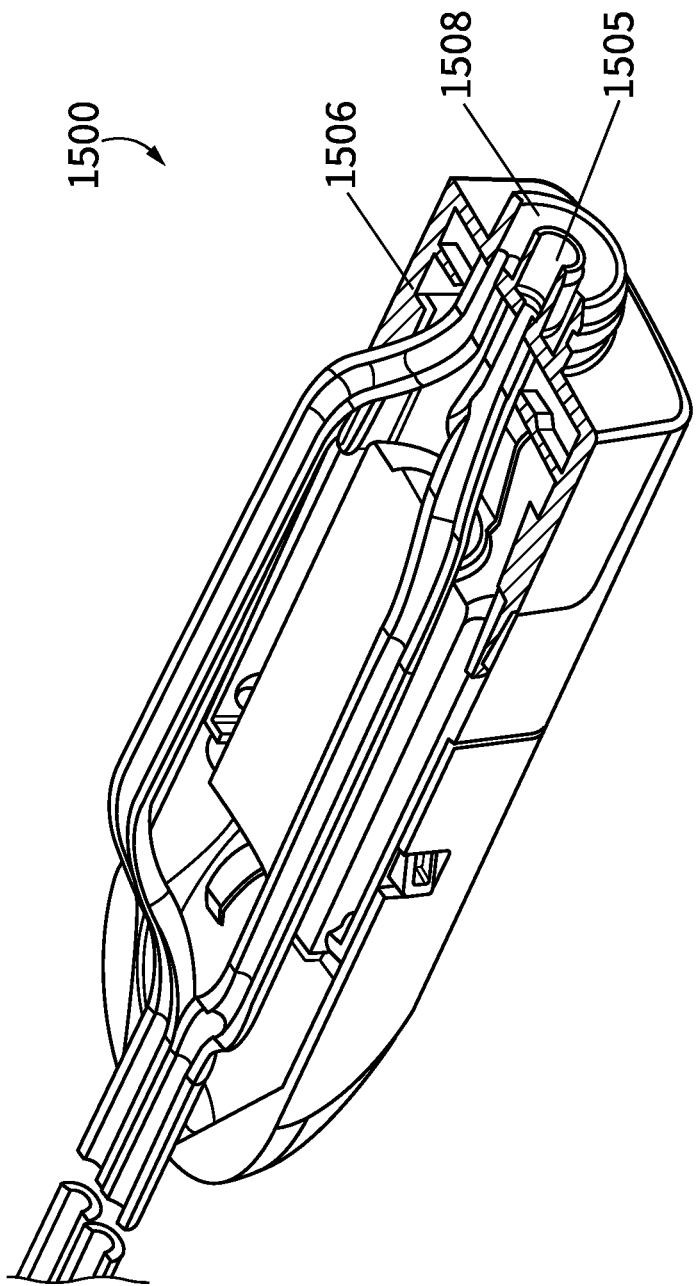
FIG. 15 shows a cutaway view of an exemplary embodiment of connection device for use with an absorbing dressing and canister and its fluid connections.

FIG. 15 shows a corresponding connector device 1500 for use with an absorbing dressing which includes a connector 1506 that connects directly to a control unit such as 901 in FIG. 9 without the need for a canister. The air outlet fitting 1505 and sensor outlet fitting 1508 connect directly to the control unit, such as 901 in FIG. 9 via the connector 907.

Methods of Use

In one aspect of the disclosure, provided herein are methods for replacing a fluid retention source during NPWT using connectors and connecting devices described herein. An exemplary method for replacing a fluid retention source generally comprises (a) providing a NPWT system comprising a first connector connected to both a control unit and a first fluid retention source, (b) disconnecting the first connector from the control unit and the first fluid retention source, in either order, and (c) connecting a second connector to a second fluid retention source and the control unit, in either order. In some embodiments, the control unit comprises a source of negative pressure, a first connection site in fluid communication with the source of negative pressure, a sensor, and a second connection site in fluid communication with the sensor. In some embodiments, the first connector is connected to the first connection site and the second connection site of the control unit. In some embodiments, the first connector and the second connector each comprise an air outlet fitting and an air inlet fitting connected by an air pathway, and a sensor outlet fitting and a sensor inlet fitting connected by a sensor pathway. In some embodiments, the first connection site of the control unit is connected to the air outlet fitting of the first connector in step (a) and the air outlet fitting of the second connector in step (c). In some embodiments, the second connection site of the control unit is connected to the sensor outlet fitting of the first connector in step (a) and the sensor outlet fitting of the second connector in step (c). In some embodiments, the first fluid retention source is connected to the air inlet fitting of the first connector in step (a), and the second fluid retention source is connected to the air inlet fitting of the second connector in step (c). In some embodiments, if a liquid is located within the first connector, when the first connector is disconnected from the first fluid retention source, the liquid is retained within the first connector.

In some embodiments, the first fluid retention source is a first canister and the second fluid retention source is a second canister. In some cases, the first connector and the second connector each further comprise a fluid inlet fitting and a fluid outlet fitting connected by a fluid pathway; and connection of the first canister to the first connector provides fluid communication between the fluid outlet fitting and the air inlet fitting of the first connector, and connection of the second canister to the second connector provides fluid communication between the fluid outlet fitting and the air inlet fitting of the second connector. In some cases, the fluid inlet fitting of the first connector is connected to a transfer dressing.

In some embodiments, the first fluid retention source is a first absorbent dressing and the second fluid retention source is a second absorbent dressing. In some cases, the air inlet fitting of the first connector is connected to the first absorbent dressing by a first air supply tube and the air inlet fitting of the second connector is connected to the second absorbent dressing by a second air supply tube.

In some embodiments, the first fluid retention source is a canister and the second fluid retention source is an absorbent dressing. In some cases, the first connector further comprises a fluid inlet fitting and a fluid outlet fitting connected by a fluid pathway; and wherein connection of the canister to the first connector provides fluid communication between the fluid outlet fitting and the air inlet fitting of the first connector. In some cases, the fluid inlet fitting of the first connector is connected to a transfer dressing by a fluid supply tube. In some cases, the fluid inlet fitting of the first connector is connected to a fluid retention dressing by a fluid supply tube. In some cases, the air inlet fitting of the second connector is connected to the absorbent dressing by an air supply tube.

In some embodiments, the first fluid retention source is an absorbent dressing and the second fluid retention source is a canister. In some cases, the second connector further comprises a fluid inlet fitting and a fluid outlet fitting connected by a fluid pathway; and wherein connection of the canister to the second connector provides fluid communication between the fluid outlet fitting and the air inlet fitting of the first connector. In some cases, the fluid inlet fitting of the second connector is connected to a transfer dressing by a fluid supply tube. In some cases, the fluid inlet fitting of the second connector is connected to a fluid retention dressing by a fluid supply tube. In some cases, the air inlet fitting of the first connector is connected to the absorbent dressing by an air supply tube.

In some embodiments, the first connector is housed in a first connecting device and the second connector is housed in a second connecting device, the first connecting device and second connecting device each further comprising a power source. In some cases, the power source provides power to the source of negative pressure when the first connector and the second connector are connected to the control unit. In some cases, the air outlet of the first connector and the air outlet of the second connector each comprise an electrical contact for providing power to the control unit. In some embodiments, the method further comprises removing the power source from the first connecting device and recycling the power source.

The following examples are provided to further illustrate the advantages and features of the present disclosure, but are not intended to limit the scope of the disclosure. While they are typical of those that might be used, other configurations, procedures, or techniques known to those skilled in the art may alternatively be used.

EXAMPLES

Example 1: Connecting Device and NPWT System

A control unit for use with a NPWT system was manufactured to supply negative pressure in systems using either an absorbing dressing or a transfer dressing and canister. The control unit is configured to connect with: the absorbing dressing via a first connector, and the transfer dressing and canister via a second connector. The control unit comprises a first connection site adapted to connect with an air outlet fitting of both the first and second connectors. The first connection site communicates with a diaphragm pump housed within the device. A general depiction of the control unit is represented by 320 in FIG. 3 or 620 in FIG. 6.

A connecting device for housing the first connector and second connector was manufactured. In use, the air outlet fitting of the first connector or second connector is mated with the first connection site of the control unit. Each connector further comprises an air inlet fitting in communication with the air outlet fitting via an air pathway. A general depiction of the connecting device housing is represented by 310 in FIG. 3 or 610 in FIG. 6.

The control unit mated with the connecting device via the first or second connector has a length of about 130-150 mm, a width of about 50-80 mm, and a height of about 16-20 mm.

Figure 7:
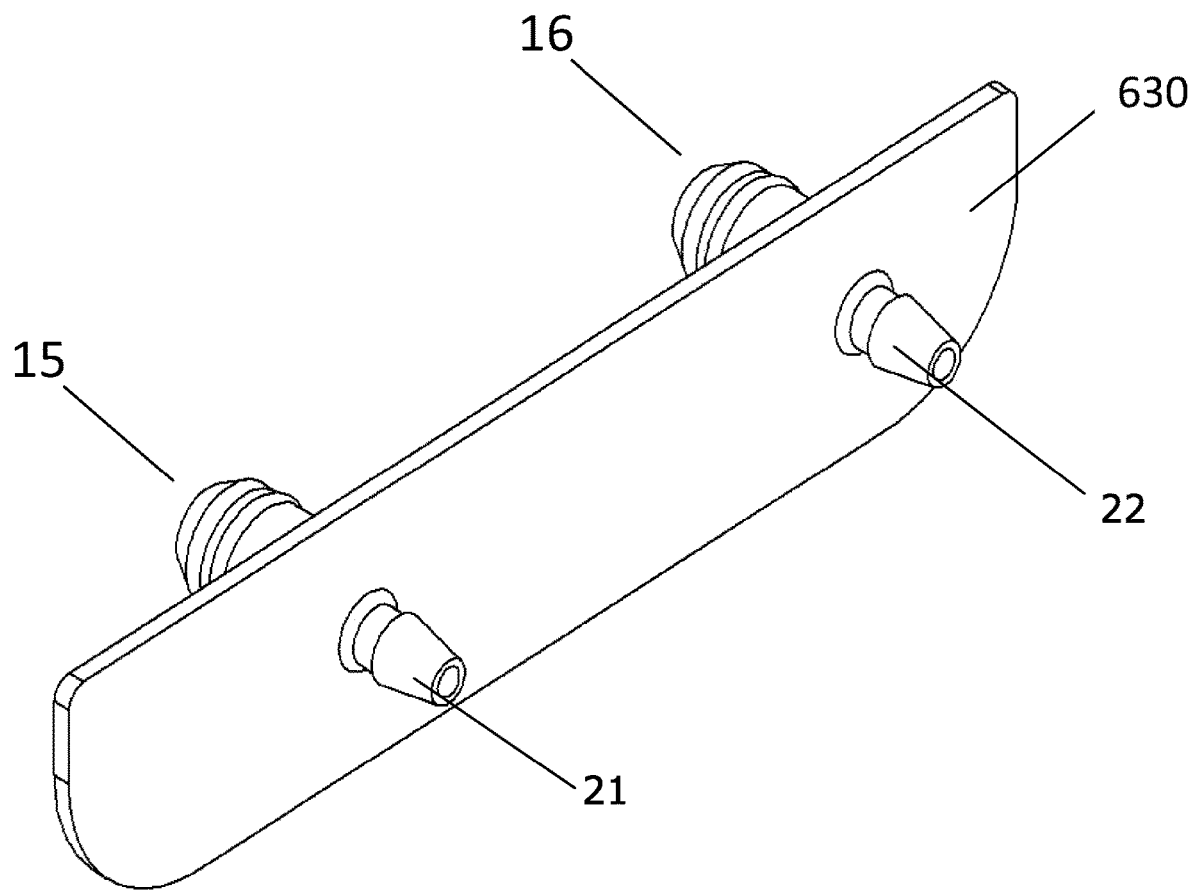
FIG. 7 shows a detailed view of the connector 630 of FIG. 6.

The first connector has the general configuration of the connector shown in FIG. 7; however, the first connector does not require all features of the connector shown in FIG. 7. For example, some first connectors made do not comprise a fitting for a sensor (16, 22). The first connector has a length of about 15-30 mm, a width of about 50-80 mm, and a height of about 15-20 mm.

The second connector further comprises a fluid inlet fitting connected by a fluid pathway to a fluid outlet fitting, and an air inlet fitting connected by an air pathway to the air outlet fitting; wherein the fluid outlet fitting is in fluid communication with the air inlet fitting upon joining the fluid outlet fitting and the air inlet fitting the canister. The second connector has the general configuration of the connector shown in FIG. 4, however, the second connector does not require all features of the connector shown in FIG. 4. For example, some second connectors do not comprise a fitting for a sensor (16, 13). The second connector has a length of about 15-30 mm, a width of about 50-80 mm, and a height of about 15-20 mm.

Example 2: Connecting Device Comprising a Power Source

The connecting device of Example 1 comprises a power source. The power source is sometimes dependent on the type of connector of the device. For a first connector for use with an absorbent dressing, the power source may require less power than a second connector for use with a transfer dressing and canister, where a greater amount of exudate is collected over time. Thus, the connecting device is tunable depending on its use. Further, the power source is optionally removable and/or replaceable.

A connecting device was manufactured having a CR123a lithium manganese primary cell. This provides the diaphragm pump with energy for use in a NPWT for about 4 to 8 days. The duration is dependent on, for example, the exudate rate of the wound and the air leak rate of the dressing used.

Example 3: Method of Replacing a Wound Dressing

A patient presents with an exudating wound requiring collection of exudates with a canister during a NPWT. A transfer dressing is sealed around the perimeter of the wound site. The transfer dressing is connected to the canister and control unit via the connecting device of Example 1, having the second connector. A negative pressure of between about 80 and 125 mmHg below atmospheric pressure is applied to the wound site. Exudates are drawn from the wound site to the second connector via a fluid tube connecting an opening of the transfer dressing to the fluid inlet fitting of the second connector. The exudates pass through the second connector and into the canister. The canister is optionally replaced by disconnecting the second connector from the control unit, where upon disconnection, the negative pressure in the system prevents exudates from leaking from the device housing the second connector. An additional dressing, canister, and second connector are supplied and the NPWT continues.

When the exudating wound can be managed using an absorbent dressing, the additional second connector is disconnected from the control unit as before. A second connecting device of Example 1, having the first connector, is supplied to the patient with an absorbent wound dressing configured to retain exudates removed from the wound during NPWT. The second connecting device is designed in a manner such that the patient can only connect the device to the absorbent wound dressing. The patient connects the second connecting device to the control unit via the air outlet fitting of the first connector, and to the absorbent dressing via the air inlet fitting connected to the absorbent dressing by a tubing. The patient optionally replaces the absorbent dressing and second connecting device as needed during the therapy.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. A device for use in negative pressure wound therapy comprising:
   a) a first compartment comprising a first connection site, and
   b) a connector comprising an air inlet and an air outlet connected by an air pathway, wherein the air outlet is connectable to the first connection site, wherein the connector is further selected from:
      i) a first connector, wherein the air inlet of the first connector is connectable to a first fluid retention source; and
      ii) a second connector further comprising a fluid inlet and a fluid outlet connected by a fluid pathway, wherein the air inlet and the fluid outlet of the second connector are connectable to a second fluid retention source, and the fluid inlet connectable with a transfer dressing or a fluid retention dressing;
      wherein the first connector and second connector interchangeably connect to the first connection site of the device.

2. The device of claim 1, wherein the first compartment further comprises a second connection site individually connectable to a sensor outlet of the first connector and a sensor outlet of the second connector, wherein the first connector and second connector each further comprise a sensor inlet and a sensor pathway connecting the sensor outlet and the sensor inlet fitting.

3. The device of claim 2, wherein the first connection site and the second connection site are positioned on a first side of the device.

4. The device of claim 1, wherein the first fluid retention source is an absorbent wound dressing.

5. The device of claim 1, wherein the fluid pathway of the second connector is configured to retain a liquid when the fluid outlet of the second connector is not connected to the second fluid retention source.

6. The device of claim 1, wherein the second fluid retention source is a canister.

7. The device of claim 1, wherein the air outlet or the first connection site comprises a sealing member configured to provide a sealed connection between the air outlet and the first connection site.

8. The device of claim 7, wherein the sealing member is an O-ring.

9. The device of claim 2, wherein the sensor outlet or the second connection site comprises a sealing member configured to provide a sealed connection between the sensor outlet and the second connection site.

10. The device of claim 9, wherein the sealing member is an O-ring.

11. A system comprising the device of claim 1, and a second compartment, wherein the first compartment and second compartment are connectable individually via the first connector and the second connector.

12. The device of claim 11, wherein the first connection site is configured to be in fluid communication with a source of negative pressure.

13. The device of claim 12, wherein the first compartment comprises the source of negative pressure.

14. The device of claim 1, wherein the first compartment of the device comprises a pressure sensor.

15. The device of claim 11, wherein the second compartment comprises a power source.

16. A method for replacing a fluid retention source during negative pressure wound therapy, the method comprising:
   a) obtaining
      i) a control unit comprising a source of negative pressure, a first connection site in fluid communication with the source of negative pressure, a sensor, and a second connection site in communication with the sensor;
      ii) a first connector connected to the first connection site and the second connection site of the control unit; and
      iii) a first fluid retention source connected to the first connector;
   b) disconnecting the first connector from the control unit and the first fluid retention source, in either order;
   c) connecting a second connector to: a second fluid retention source, and the first connection site and the second connection site of the control unit; wherein the second connector is connected to the second fluid retention source and control unit in either order;
      wherein the first connector and the second connector each comprise an air outlet and an air inlet connected by an air pathway, and a sensor outlet and a sensor inlet connected by a sensor pathway;
      wherein the first connection site of the control unit is connected to the air outlet of the first connector in step (a) and the air outlet of the second connector in step (c);
      wherein the second connection site of the control unit is connected to the sensor outlet of the first connector in step (a) and the sensor outlet of the second connector in step (c); and
      wherein the first fluid retention source is connected to the air inlet of the first connector in step (a), and the second fluid retention source is connected to the air inlet of the second connector in step (c).

17. The method of claim 16, wherein the first fluid retention source is a first canister and the second fluid retention source is a second canister.

18. The method of claim 16, wherein the first fluid retention source is a first absorbent dressing and the second fluid retention source is a second absorbent dressing.

19. The method of claim 16, wherein the first fluid retention source is a canister and the second fluid retention source is an absorbent dressing, or the first fluid retention source is an absorbent dressing and the second fluid retention source is a canister.

20. The method of claim 16, wherein the first connector is housed in a first connecting device and the second connector is housed in a second connecting device, the first connecting device and second connecting device each further comprising a power source.

* * * * *